US012807927B2

(12) United States Patent
El-Harane et al.

(10) Patent No.: US 12,807,927 B2
(45) Date of Patent: Nov. 24, 2026

(54) METHODS OF PRODUCING CELL SPHEROIDS AND TOOL THEREFORE

(71) Applicants: UNIVERSITE DE GENEVE, Geneva (CH); LES HOPITAUX UNIVERSITAIRES DE GENEVE, Geneva (CH)

(72) Inventors: Sanae El-Harane, Tulette (FR); Olivier Preynat-Seauve, Habère-Lullin (FR); Karl-Heinz Krause, Geneva (CH); Stéphane Durual, Yvoire (FR); Ali Modarressi, Anières (CH); Thomas Braschler, Chavannes-Près-Renens (CH)

(73) Assignees: UNIVERSITE DE GENEVE, Geneva (CH); LES HÔPITAUX UNIVERSITAIRES DE GENÈVE, Geneva (CH)

( * ) Notice: Subject to any disclaimer, the term of this patent is extended or adjusted under 35 U.S.C. 154(b) by 482 days.

(21) Appl. No.: 18/272,815

(22) PCT Filed: Jan. 17, 2022

(86) PCT No.: PCT/EP2022/050920

§ 371 (c)(1),
(2) Date: Jul. 18, 2023

(87) PCT Pub. No.: WO2022/152916

PCT Pub. Date: Jul. 21, 2022

(65) Prior Publication Data

US 2024/0301357 A1 Sep. 12, 2024

(30) Foreign Application Priority Data

Jan. 18, 2021 (EP) .................................... 21152106

(51) Int. Cl.
*C12N 5/0775* (2010.01)
*C12N 5/074* (2010.01)
*C12N 5/0797* (2010.01)

(52) U.S. Cl.
CPC ......... *C12N 5/0667* (2013.01); *C12N 5/0623* (2013.01); *C12N 5/0696* (2013.01); *C12N 2513/00* (2013.01); *C12N 2533/30* (2013.01); *C12N 2535/10* (2013.01); *C12N 2539/00* (2013.01)

(58) Field of Classification Search
CPC .. C12N 5/0667; C12N 5/0623; C12N 5/0696; C12N 2513/00; C12N 2533/30; C12N 2535/10; C12N 2539/00; C12N 2506/02; C12N 2506/08; C12N 2533/74; C12N 2533/76; C12N 2533/78; C12N 2533/80; C12N 5/0062; C12N 5/0068; C12N 5/0606; C12N 5/0619; C12N 5/0697; C12N 5/0653; C12M 23/20; C12M 23/12; C12M 25/02; B01L 2200/0668; B01L 2200/12; B01L 2300/163; B01L 3/5085
See application file for complete search history.

(56) References Cited

U.S. PATENT DOCUMENTS

2019/0382701 A1* 12/2019 Apfel .................... C12M 23/12

FOREIGN PATENT DOCUMENTS

| | | |
|---|---|---|
| EP | 3 296 018 | 3/2018 |
| WO | WO 2016/103002 | 6/2016 |
| WO | WO 2019/010587 | 1/2019 |
| WO | WO 2019/145847 | 8/2019 |

OTHER PUBLICATIONS

El Harane, S. et al. "Generation of Individualized, Standardized, and Electrically Synchronized Human Midbrain Organoids" *Cells*, Aug. 6, 2025, pp. 1-26, vol. 14, No. 1211.
Written Opinion in International Application No. PCT/EP2022/050920, Apr. 13, 2022, pp. 1-10.
Abberton, K. M. et al. "Myogel, a Novel, Basement Membrane-Rich, Extracellular Matrix Derived from Skeletal Muscle, Is Highly Adipogenic in vivo and in vitro" *Cell Tissues Organs*, published online Mar. 20, 2008, pp. 347-358, vol. 188.
Alimperti, S. et al. "Serum-free spheroid suspension culture maintains high proliferation and differentiation potentials of mesenchymal stem cells" *Biotechnology Progress*, 2014, pp. 1-18, vol. 30, No. 4.
Alvarez-Pérez, J. et al. "Microscopic images of intraspheroidal pH by $^1$H magnetic resonance chemical shift imaging of pH sensitive indicators" *MAGMA*, published online Nov. 18, 2005, pp. 293-301, vol. 18.
Anada, T. et al. "An oxygen-permeable spheroid culture system for the prevention of central hypoxia and necrosis of spheroids" *Biomaterials*, available online Aug. 30, 2012, pp. 8430-8441, vol. 33.
Augustyniak, J. et al. "Organoids are promoting tools for species-specific in vitro toxicological studies" *Journal of Applied Toxicology*, 2019, pp. 1610-1622, vol. 39.
Baraniak, P. R. et al. "Scaffold-free culture of mesenchymal stem cell spheroids in suspension preserves multilineage potential" *Cell and Tissue Research*, Mar. 2012, pp. 1-19, vol. 347, No. 3.
Bhang, S. H. et al. "Transplantation of Cord Blood Mesenchymal Stem Cells as Spheroids Enhances Vascularization" *Tissue Engineering: Part A*, 2012, pp. 2138-2147, vol. 18, Nos. 19-20.

(Continued)

*Primary Examiner* — Titilayo Moloye
(74) *Attorney, Agent, or Firm* — SALIWANCHIK, LLOYD & EISENSCHENK

(57) ABSTRACT

The present invention is directed to a substrate material for the formation of cell spheroids/organoids and uses thereof. The invention further relates to methods of preparation of such a substrate material and related tools and uses thereof, methods using such a substrate material for the formation of cell spheroids and resulting spheroids and uses thereof.

7 Claims, 18 Drawing Sheets

(56) References Cited

OTHER PUBLICATIONS

Bourin, P. et al. "Stromal cells from the adipose tissue-derived stromal vascular fraction and culture expanded adipose tissue-derived stromal/stem cells: a joint statement of the International Federation for Adipose Therapeutics (IFATS) and Science and the International Society for Cellular Therapy (ISCT)" *Cytotherapy*, Jun. 2013, pp. 1-14, vol. 15, No. 6.
Campos, L. S. "Neurospheres: Insights Into Neural Stem Cell Biology" *Journal of Neuroscience Research*, published online Oct. 25, 2004, pp. 761-769, vol. 78.
Cha, J. M. et al. "Efficient scalable production of therapeutic microvesicles derived from human mesenchymal stem cells" *Scientific Reports*, published online Jan. 19, 2018, pp. 1-16, vol. 8, No. 1171.
Cho, R. J. et al. "Human adipose-derived mesenchymal stem cell spheroids improve recovery in a mouse model of elastase-induced emphysema" *BMB Reports*, 2017, pp. 79-84, vol. 50, No. 2.
Cosset, E. et al. "Human Neural Organoids for Studying Brain Cancer and Neurodegenerative Diseases" *Journal of Visualized Experiments*, Jun. 28, 2019, pp. 1-8, vol. 148, e59682.
Daquinag, A. C. et al. "Adipose Tissue Engineering in Three-Dimensional Levitation Tissue Culture System Based on Magnetic Nanoparticles" *Tissue Engineering: Part C*, 2013, pp. 336-344, vol. 19, No. 5.
Di Stefano, A. B. et al. "Spheroids from adipose-derived stem cells exhibit an miRNA profile of highly undifferentiated cells" *Journal of Cellular Physiology*, 2018, pp. 8778-8789, vol. 233.
El Harane, S. et al. "Adipose-derived stem cell spheroids are superior to single-cell suspensions to improve fat autograft long-term survival" *Journal of Cellular and Molecular Medicine*, 2022, pp. 1421-1433, vol. 26.
El Harane, S. et al. "A novel and unique technology to produce human brain organoids in an air-liquid interface: characterization at the moledular, cellular and functional levels" poster presented in a keystone congress, Feb. 6, 2023, p. 1.
Feng, J. et al. "An injectable non-cross-linked hyaluronic-acid gel containing therapeutic spheroids of human adipose-derived stem cells" *Scientific Reports*, published online May 8, 2017, pp. 1-13, vol. 7, No. 1548.
Furuhata, Y. et al. "Small spheroids of adipose-derived stem cells with time-dependent enhancement of IL-8 and VEGF-A secretion" *Genes to Cells*, 2016, pp. 1380-1386, vol. 21.
Gorkun, A. A. et al. "Angiogenic potential of spheroids from umbilical cord and adipose-derived multipotent mesenchymal stromal cells within fibrin gel" *Biomedical Materials*, May 21, 2018, pp. 1-10, vol. 13, No. 044108.
Gottlieb, D. I. "Large-Scale Sources of Neural Stem Cells" *Annual Review of Neuroscience*, 2002, pp. 381-407, vol. 25.
Gracz, A. D. et al. "A high-throughput platform for stem cell niche co-cultures and downstream gene expression analysis" *Nature Cell Biology*, published online Feb. 9, 2015, pp. 340-349, supplemental information pp. 1-20, vol. 17, No. 3.
Groebe, K. et al. "On the Relation Between Size of Necrosis and Diameter of Tumor Spheroids" *International Journal of Radiation Oncology, Biology, Physics*, 1996, pp. 395-401, vol. 34, No. 2.
Gwon, K. et al. "Heparin-hyaluronic acid hydrogel in support of cellular activities of 3D encapsulated adipose derived stem cells" *Acta Biomaterialia*, available online Dec. 5, 2016, pp. 284-295, vol. 49.
Hassanpour, M. et al. "Distinct role of autophagy on angiogenesis: highlights on the effect of autophagy in endothelial lineage and progenitor cells" *Stem Cell Research & Therapy*, 2018, pp. 1-16, vol. 9, No. 305.
Jeon, O. et al. "Dual-crosslinked hydrogel microwell system for formation and culture of multicellular human adipose tissue-derived stem cell spheroids" *Journal of Materials Chemistry B*, May 28, 2016, pp. 1-16, vol. 4, No. 20.
Kapur, S. K. et al. "Human adipose stem cells maintain proliferative, synthetic and multipotential properties when suspension cultured as self-assembling spheroids" *Biofabrication*, Jun. 2012, pp. 1-28, vol. 4, No. 2.
Kim, Y. et al. "Incorporation of gelatin microparticles on the formation of adipose-derived stem cell spheroids" *International Journal of Biological Macromolecules*, available online Jan. 31, 2018, pp. 472-478, vol. 110.
Kim, S. et al. "Combination of MSC spheroids wrapped within autologous composite sheet dually protects against immune rejection and enhances stem cell transplantation efficacy" *Tissue and Cell*, 2018, pp. 93-103, vol. 53.
Kim, S. et al. "Hydrogels with an embossed surface: An all-in-one platform for mass production and culture of human adipose-derived stem cell spheroids" *Biomaterials*, 2019, pp. 198-212, vol. 188.
Lee, Y. B. et al. "Engineering spheroids potentiating cell-cell and cell-ECM interactions by self-assembly of stem cell microlayer" *Biomaterials*, available online Mar. 1, 2018, pp. 105-120, vol. 165.
Li, M. et al. "Therapeutic Potential of Adipose-derived Stem Cell-based Microtissues in a Rat Model of Stress Urinary Incontinence" *Urology*, 2016, pp. 277e1-277e7, vol. 97.
Lombardi, F. et al. "Secretome of Adipose Tissue-Derived Stem Cells (ASCs) as a Novel Trend in Chronic Non-Healing Wounds: An Overview of Experimental In Vitro and In Vivo Studies and Methodological Variables" *International Journal of Molecular Sciences*, Jul. 30, 2019, pp. 1-18, vol. 20, No. 3721.
Mineda, K. et al. "Therapeutic Potential of Human Adipose-Derived Stem/Stromal Cell Microspheroids Prepared by Three-Dimensional Culture in Non-Cross-Linked Hyaluronic Acid Gel" *Stem Cells Translational Medicine*, published online Oct. 22, 2015, pp. 1511-1522, vol. 4.
Mirab, F. et al. "Preparation and characterization of size-controlled glioma spheroids using agarose hydrogel microwells" *PLoS ONE*, Jan. 24, 2019, pp. 1-12, vol. 14, No. 1.
Napolitano, A. P. et al. "Dynamics of the Self-Assembly of Complex Cellular Aggregates on Micromolded Nonadhesive Hydrogels" *Tissue Engineering*, 2007, pp. 2087-2094, vol. 13, No. 8.
Rettinger, C. L. et al. "Scaffold-Free, Size-Controlled Three-Dimensional Culture of Rabbit Adipose-Derived Stem Cells" *Adipose-Derived Stem Cells: Methods and Protocols*, Methods in Molecular Biology, Chapter 3, 2018, Bruce A. Bunnell and Jeffrey M. Gimble (eds.), pp. 21-30, vol. 1773.
Salo, T. et al. "A novel human leiomyoma tissue derived matrix for cell culture studies" *BMC Cancer*, 2015, pp. 1-16, vol. 15, No. 981.
Si, Z. et al. "Adipose-derived stem cells: Sources, potency, and implications for regenerative therapies" *Biomedicine & Pharmacology*, 2019, pp. 1-6, vol. 114, No. 108765.
Takahashi, J. "Stem Cell Therapy for Parkinson's Disease" *Ernst Schering Res Found Workshop*, 2006, pp. 229-244 and supplemental pp. 1-5, vol. 60.
Tieng, V. et al. "Engineering of Midbrain Organoids Containing Long-Lived Dopaminergic Neurons" *Stem Cells and Development*, 2014, pp. 1535-1547, vol. 23, No. 13.
Xu, Y. et al. "3D spheroid culture enhances survival and therapeutic capacities of MSCs injected into ischemic kidney" *Journal of Cellular and Molecular Medicine*, 2016, pp. 1203-1213, vol. 20, No. 7.
Zanoni, M. et al. "Modeling neoplastic disease with spheroids and organoids" *Journal of Hematology & Oncology*, 2020, pp. 1-15, vol. 13, No. 97.
Zhang, Q. et al. "Three-Dimensional Spheroid Culture of Human Gingiva-Derived Mesenchymal Stem Cells Enhances Mitigation of Chemotherapy-Induced Oral Mucositis" *Stem Cells and Development*, 2012, pp. 937-947, vol. 21, No. 6.
Zhang, H.-C. et al. "Microvesicles Derived from Human Umbilical Cord Mesenchymal Stem Cells Stimulated by Hypoxia Promote Angiogenesis Both In Vitro and In Vivo" *Stem Cells and Development*, pp. 3289-3297, vol. 21, No. 18.
Zhang, S. et al. "The effects of spheroid formation of adipose-derived stem cells in a microgravity bioreactor on stemness properties and therapeutic potential" *Biomaterials*, available online Dec. 1, 2014, pp. 15-25, vol. 41.

(56) References Cited

OTHER PUBLICATIONS

Zhang, X. et al. "3D Spheroid Culture Enhances the Expression of Antifibrotic Factors in Human Adipose-Derived MSCs and Improves Their Therapeutic Effects on Hepatic Fibrosis" *Stem Cells International*, 2016, pp. 1-8, Article ID 4626073.

* cited by examiner

C

D

Down-regulation in spheroids

Up-regulation in spheroids

Figure 10 C

| Pathways involving Up-regulated genes in 3Dairliwell | NES | FDR |
|---|---|---|
| Ectoderm Differentiation (Ref hsapiens) | 1.996700 | 0.000000000 |
| Histone Modifications (Ref hsapiens) | 1.863712 | 0.000000000 |
| Wnt Signaling in Kidney Disease (Ref hsapiens) | 1.862040 | 0.002336448 |
| Canonical and Non-canonical Notch signaling (Ref hsapiens) | 1.773218 | 0.000000000 |
| Neural Crest Differentiation (Ref hsapiens) | 1.761094 | 0.000000000 |
| ID signaling pathway (Ref hsapiens) | 1.743313 | 0.004514673 |
| Wnt signaling pathway (Ref hsapiens KEGG) | 1.738345 | 0.000000000 |
| Canonical and Non-Canonical TGF-B signaling (Ref hsapiens) | 1.728292 | 0.002202643 |
| Basal cell carcinoma (Ref hsapiens KEGG) | 1.654229 | 0.007371008 |
| Breast cancer (Ref hsapiens KEGG) | 1.649962 | 0.000000000 |
| TGF-beta signaling pathway (Ref hsapiens KEGG) | 1.632514 | 0.002487562 |
| Dopaminergic Neurogenesis (Ref hsapiens) | 1.627431 | 0.011185682 |
| Differentiation of white and brown adipocyte (Ref hsapiens) | 1.601307 | 0.022624435 |
| Alcoholism (Ref hsapiens KEGG) | 1.579016 | 0.005665722 |
| Notch signaling pathway (Ref hsapiens KEGG) | 1.571921 | 0.016908212 |

METHODS OF PRODUCING CELL SPHEROIDS AND TOOL THEREFORE

CROSS-REFERENCE TO RELATED APPLICATION

This application is the U.S. national stage application of International Patent Application No. PCT/EP2022/050920, filed Jan. 17, 2022.

FIELD OF THE INVENTION

The present invention relates to substrate material for the formation of cell spheroids and their uses. The invention further relates to methods of preparation of those spheroids and uses thereof.

BACKGROUND OF THE INVENTION

Cell Spheroids have promptly gained popularity because of their ability to mimic the natural cell-to-cell and cell-to-matrix interactions, to allow cell functions closer to the in vivo situation, and to establish nutrient and oxygen gradients also replicating the original tissue. Methods showed the possibility to engineer cell spheroids, including the hanging drop method (Li et al., 2016, *Urology,* 97:277), self or forced aggregation methods (Rettinger et al., 2018, *Stem Cells. Methods Mol Biol.,* 1773:21-30), microgravity bioreactors (Zhang et al., 2015, *Biomaterials,* 41:15-25), magnetic levitation (Daquinag et al., 2013, *Tissue Eng Part C Methods,* 19(5):336-344), encapsulation in scaffolds or particles (Feng et al., 2017, *Sci Rep.* 2017; 7(1):1548; Furuhata et al., 2016, *Genes Cells.,* 21(12): 1380-1386; Gorkun et al., 2018, *Biomed Mater.,* 13(4):044108; Jeon et al., 2016, *J Mater Chem B.,* 4(20): 3526-3533; Kim et al., 2019, *Biomaterials,* 188:198-212; Kim et al., 2018, *Int J Biol Macromol.,* 110: 472-478; Mineda et al., 2015, *Stem Cells Transl Med.,* 4(12): 1511-1522). There is a clear consensus that the generation of cell spheroids, in comparison to two-dimension (2D) monolayers growing on plastic, increase their similarity with the in vivo situation. From a biotechnology point of view, many drug screening, toxicity assays and disease modelizations use cell spheroids or organoids. From a cell therapy point of view, spheroids are more attractive for the following reasons:

- Cell culture is simplified, with reduced costs, reduction of cell passages and associated quality controls. These simplifications are especially critical in a Good Medical Practice (GMP) environment;
- Volumes of cell culture media, then associated costs are reduced with spheroids compared to monolayers;
- Cell spheroids have been reported to display a better survival in vivo after transplantation (Bhang et al., 2012, *Tissue Eng Part A.,* 18(19-20): 2138-2147) and higher resistance to an oxidative environment (Zhang et al., 2012, *Stem Cells Dev.,* 21(6):937-947).
- In the case of regenerative cell therapy, spheroids of Mesenchymal Stem cells (MSC) produce a better healing secretome than MSC in single cell suspensions. MSC from fat tissue, namely Adipose-derived Stem Cells (ASC), are particularly attractive for regenerative cell therapy. Their easy availability and expansion in culture, associated with a potent regenerative, immunomodulatory and anti-fibrotic secretome (Lombardi et al., 2019, Int *J Mol Sci.,* 20(15)), make ASC one of the most promising candidates for regenerative medicine (Si et al., 2019, *Biomed Pharmacother.,* 114:108765). Focusing mainly on inflammatory and/or degenerative diseases, more than 300 clinical trials are currently registered with ASC (ClinicalTrials.gov). MSC forming spheroids harbour increased regenerative properties compared to single cells in 2D suspension in vitro (Di Stefano et al., 2018, J Cell Physiol., 233(11):8778-8789; Gwon et al., 2017, *Acta Biomater.,* 49:284-295; Kapur et al., 2012, *Biofabrication.,* 4(2):025004; Kim et al., 2018, *Tissue Cell.,* 53:93-103). In vivo, by using models of kidney degeneration (Xu et al., 2016, *J Cell Mol Med.,* 20(7): 1203-1213), hepatic fibrosis (Zhang et al., 2016, *Stem Cells Int.,* 2016:4626073) or failure (Zhang et al., 2015, supra), urinary tract degeneration (Li et al., 2016, supra), wounds (Feng et al., 2017, supra; Mineda et al., 2015, supra; Cheong et al., 1990, *Singapore Med J.,* 31(4):350-354) and lungs disease (Cho et al., 2017, *BMB Rep.,* 50(2): 79-84), MSC spheroids displayed better survival in ischemic conditions and higher resistance to oxidative stress-induced apoptosis (Zhang et al., 2012, supra).

Neoplastic diseases are also intensively modelled in vitro with spheroids and organoids to help for the discovery of new targets and treatments (Zanoni et al., 2020, Journal of Hematology & Oncology, 13:97 doi.org/10.1186/s13045-020-00931-0). Moreover, spheroids and organoids are of great interest for toxicology screening assays (Augustyniak et al., 2019, Appl Toxicol., 39(12):1610-1622).

Uniform shape, size, and cell numbers are needed for the use of cell spheroids, either in screening assays, toxicology assays, tumor modelization or manufacturing of cell therapy products. Despite the recognized advantages of cell spheroids, numerous technical limitations still strongly limit their use in screening assays and cell therapy. Hanging drop methods are heavy manual procedures not compatible with standardization and good manufacturing conditions regarding the number of cells needed for a trial. Spontaneous aggregation in low attachment plates is working but generate an uncontrolled distribution of spheroid's size, mixing small and large aggregates with a high degree of heterogeneity. This phenomenon is due to the frequent adhesion between spheroids themselves and between spheroids and plastic, strongly reducing the standardization of their production. To prevent adherence to plastic, agitation methods in immersion are insufficient to solve this problem, facilitating aggregation into larger aggregates and spheroids alterations. As standardization and purity of preparations appear as the main limitation of spheroids for all applications, encapsulation methods were developed and provide large scale and size-controlled productions (Jeon et al., 2016, supra; Kim et al., 2019; Lee et al., 2018, *Biomaterials,* 165:105-120). However, if scaffold-based approaches for cell therapy provide notably an attractive support for cell therapy applications, it also invites foreign body reactions causing inflammation and toxicity, and may also sometime interfere with the regeneration of indigenous tissue due to very slow degradation. Numerous manufacturers offer now ready-to-use microwells for forced aggregation, with the aim to generate large numbers of uniform spheroids at low cost and a minimum of time, being probably the best current option. But the major limitation of this method for MSC is the rapid adherence of MSC to the microwells, beginning at the same time than cell-to-cell aggregation, due to the high affinity of MSC with plastic. Based on this major limitation, non-adherent microwells made with agarose (Napolitano et al., 2007, *Tissue Eng.,* 13(8): 2087-2094), or polyethylene glycol hydrogels (('ha et al., 2018, *Sci Rep.,* 8(1):1171) have been developed and commercialized. The inconvenient of this method is the immersion of microwells in medium: medium change can disrupt the stability of spheroids at the bottom of each microwell and these static conditions reduce oxygen diffusion in the spheroids. Under these static conditions, a necrotic core develops (Alvarez-Perez et al., 2005, *MAGMA,* 18(6):293-301; Groebe et al., 1996, *Int J Radiat Oncol Biol Phys.,* 34(2): 395-401). At the opposite, dynamic cultivation of immersed aggregates (under agitation) less report necrotic cores (Alimperti et al., 2014, *Biotechnol Prog.,* 30(4):974-983; Baraniak et al., 2012, *Cell Tissue Res.,* 347(3): 701-711) but, at the same time, is not compatible with MSC because of the strong and rapid fusion of spheroids between themselves.

Therefore, regarding the biotechnological and clinical potential of cell spheroids, there is a strong need of more standardized and simplified manufacturing processes.

SUMMARY OF THE INVENTION

The present invention relates to the unexpected finding of a method of preparation of spheroids applicable to all types of cells forming spheroids and organoids which is simple and rapid and leads to pure, highly standardized and non-encapsulated cell spheroids. The method has been validated with ASC-spheroids, Pluripotent Stem Cells (PSC) and PSC-derived neurospheres which led to spheroids that are standardized, stable overtime and present long-lasting properties in terms of survival, stability, regeneration and homogeneity.

The method of the present invention presents several advantages of both dynamic and static conditions, without the need of any external scaffolds as opposed to known methods. The simplicity (minimum of intervention, less culture medium required) and the very high level of standardization of this method open a realistic possibility for the transfer of the use of spheroids to the clinics and for screening assays at very reasonable costs.

An object of this invention is to provide a substrate material allowing the simple and rapid preparation of spheroids in an efficient, accurate and reliable manner and a method of preparation of said substrate material.

It is advantageous to provide a method for the preparation of a substrate allowing the preparation of spheroids which can be easily customized to lead to a substrate material which is adequate for the type of cells used in the formation of spheroids and the wished size of the formed spheroids.

It is advantageous to provide a substrate material allowing the preparation of spheroids which can be easily transported and stored in a cost-effective manner.

It is advantageous to provide a ready-for use substrate material allowing the preparation of spheroids.

Another object of the invention is to provide a method for the preparation of spheroids that enables obtaining spheroids of various types of cells in an efficient, accurate and reliable manner.

It is advantageous to provide a method for the preparation of spheroids that can be adapted to the nature of the cells used in this preparation and the size of the needed spheroids or organoids.

It is advantageous to provide a method for the preparation of spheroids that allows the preparation of spheroids having standardized characteristics (size & shape).

It is advantageous to provide a method for the preparation of spheroids that allows the preparation of spheroids in a cost and time effective manner.

It is advantageous to provide a method for the preparation of spheroids that allows the preparation of spheroids which are stable allowing long-term cultures.

It is advantageous to provide a method for the preparation of spheroids that allows the preparation of spheroids from MSC and ASCs with high regenerative properties.

Another object of the invention is to provide spheroids from various types of cells having standardized characteristics (size & shape) and long-term stable properties.

It is advantageous to provide spheroids from ASCs useful for tissue regeneration or biological tissue culture (in vitro or ex-vivo) and tissue engineering or cosmetic applications.

It is advantageous to provide spheroids from ASCs which actively produces high amounts of wound healing factors and any material containing those.

It is advantageous to provide a method for the preparation of spheroids that allows the preparation of neurospheres, in particular useful for the modelization of neural tissue or for use in cell replacement therapies.

Another object of the invention is to provide a kit for the preparation of a substrate material allowing the preparation of spheroids in an efficient, accurate and reliable manner.

It is advantageous to provide a kit that allows the preparation of a substrate material for the preparation of spheroids that is adequate for the type of cells used in the formation of spheroids and the wished size of the formed spheroids.

Another object of the invention is to provide a kit for the preparation of spheroids in an efficient, accurate and reliable manner.

It is advantageous to provide a kit that allows the preparation of spheroids that is specific for the type of cells used in the formation of spheroids and the aimed size of the formed spheroids.

Objects of this invention have been achieved by providing a method and substrate materials, a method for the preparation of spheroids and uses thereof, cell spheroids, a die for the preparation of a substrate material for cell culture, a kit for the preparation of a substrate material or for the preparation of spheroids as disclosed herein.

Disclosed herein, according to a first aspect of the invention, is a method for the preparation of a substrate material for cell culture, said method comprising the following steps:

a) Providing a semipermeable membrane supported by a support frame on its edges;
b) Forming a malleable layer of hydrophilic and porous material on said semipermeable membrane to form a composite matrix;
c) Pressing a hydrophobic die comprising a plurality of tapered protuberances into an outer surface of the malleable layer of hydrophilic material of said composite matrix to form a plurality of well-shaped indents in said layer;
d) Removing the die from the layer of hydrophilic material to obtain an imprinted composite matrix comprising a hydrophilic material layer with a plurality of lasting well-shaped indents on its outer surface supported by a semipermeable membrane on its inner surface.

According to another aspect of the invention, is provided a substrate material for the preparation of spheroids wherein said material comprises: a hydrophilic and porous material layer with a plurality of lasting well-shaped indents on its outer surface supported by a semipermeable membrane on its inner surface, wherein said well-shaped indents have an aperture from 1 $\mu m^2$ to 1 $mm^2$ and a bottom surface from about 1 $\mu m^2$ to 1 $mm^2$.

According to another aspect of the invention, is provided a use of a substrate material according to the invention for the preparation of spheroids.

According to another aspect of the invention, is provided a method for the preparation of spheroids, said method comprising the following steps:

i) Providing a spheroid culture medium in a cell culture vessel;

ii) Placing a substrate material comprising a hydrophilic and porous material layer with a plurality of lasting well-shaped indents on its outer surface supported by a semipermeable membrane on its inner surface (on the surface of a culture medium such that the substrate material is floating on the surface of a culture medium;

iii) Contacting a cell suspension with the surface of the floating substrate material until cells forms spheroids on the surface of the floating substrate material.

According to another aspect of the invention, is provided spheroids obtainable from a method according to the invention having standardized characteristics (size/shape homogeneity) and long-term stable properties free from necrotic cores. The absence of necrotic core can be assessed by flow cytometry, histology, ATP measurement, staining with fluorescent probes.

According to another aspect of the invention, is provided spheroids according to the invention for use in cell therapy or in the preparation of a cell tissue useful for regenerative or replacement therapies or a cell substrate useful for in vitro assays.

According to another aspect of the invention, is provided the use of spheroids for the preparation of a cell material, a tissue or a cellular substitute useful in regenerative or replacement therapies or as substrate for in vitro assays.

According to another aspect of the invention, is provided a cell material, a tissue or a cellular substitute comprising spheroids according to the invention (e.g. a cell therapy material/tissue, a cell substrate for screening assays, toxicological studies, a cell material/tissue for healthy or diseased tissue modelization).

According to another aspect of the invention, is provided a die for the preparation of a substrate material for cell culture, said die comprises a handle and a patterning surface, said patterning surface having a size from about 5 mm to 10 cm, being made of a hydrophilic material and comprising a plurality of tapered protuberances (e.g. of triangular or spheroidal or linear or pyramidal shape), wherein said tapered protuberances have base surface area from 20 μm to 2 mm and a tip surface area from 1 $mm^2$ to 100 $cm^2$.

According to another aspect of the invention, is provided a kit for the preparation of a substrate material allowing the preparation of spheroids in an efficient, accurate and reliable manner, said kit comprising at least one die according to the invention and instructions for use.

According to another aspect of the invention, is provided a kit for the preparation of spheroids, said kit comprising at least one substrate material according to the invention and instructions for use.

According to another aspect of the invention, is provided a method for the regeneration of a biological tissue from a subject, said method comprising contacting one or more individualized cell spheroids with said biological tissue.

DETAILED DESCRIPTION

The cells suitable according to the invention include Mesenchymal Stem Cells, Adipose-derived Stem Cells, hepatocytes, cardiomyocytes, chondrocytes, neural cells, neurons, astrocytes, oligodendrocytes, pluripotent stem cells, iPS, embryoid bodies, skin cells, lung epithelial cells, all tumor cells such as breast cancer cells, hepatic cells, pancreatic cells, intestinal cells, epidermal cells, keratinocytes or bone cells or a mixture of two or more cell types to the above list.

Suitable cells according to the invention also include in particular fibroblasts, endothelial cells, immune cells, muscle cells, blood cells, vascular cells, multipotent stem cells, unipotent stem cells, and in general adherent or non-adherent cells.

A cellular material according to the invention relates to a material which comprises cells or which is prepared from cells such as tissue or cellular substitutes, a cell assay substrate or a pharmaceutical or cosmetic composition comprising cells.

The term "tissue substitute" or "cellular substitute" relates to a substitute material which may replace native tissue or cells from a subject that have been damaged. In a particular embodiment, tissue or cellular substitutes according to the invention include skin substitutes neuronal substitutes and visceral tissue substitutes.

The term spheroid refers to three-dimensional cellular modeling that better reproduce the environmental conditions of the in vivo situation compared to a two-dimensional cellular model, especially with cell-cell and cell-matrix interactions. It encompasses "organoids", "microtissues" and in general "cellular aggregates" grown in three dimensions.

The term "spheroid culture medium" refers to a cell culture medium suitable for the formation of spheroids. It includes a cell culture medium for cell culture maintenance which comprises one or more bioactive factors that promote cell proliferation, differentiation, self-organization, maturation or maintenance of spheroids/organoids. Bioactive factors are preferably small molecules, chemical compounds, extracellular matrix factors, proteins of major signaling pathways, proteoglycans, non-proteoglycan polysaccharide, fibrous proteins or extracellular matrix components. Typical spheroid culture medium and suitable bioactive factors are described in Examples 4 and 5 or in Tieng et al., 2014, *Stem Cells and Development,* 1535-1547.

The expression "semi-permeable membrane" refers to a membrane that allows the passage of solvent as well as a fraction of the solutes. It allows the preferential passage of certain substances present in a solution compared to others, depending on the size of the pores. It encompasses hydrophilic membranes, filter membranes and porous membranes. Example of those are provided herein.

Method of Preparation of a Substrate Material According to the Invention

Figure 1A:
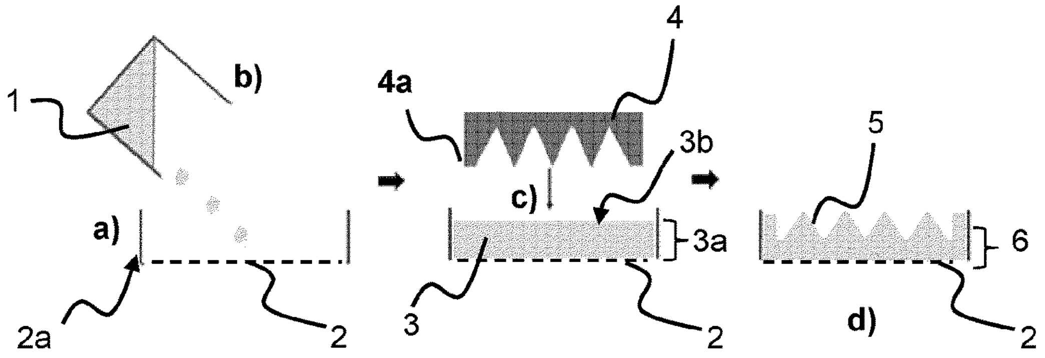
FIG. 1 provides a schematic representation of the main steps of a method for preparing a substrate material according to the invention (A) and pictures the resulting substrate material of the invention at the end of step d) (B) and of step e) (C) as described in Example 1.

Referring to the figures, in particular first to FIG. 1A, is provided an illustration of a method for preparation of a substrate material for cell culture comprising the steps of:

a) Providing a semipermeable membrane (2) supported by a support frame on its edges (2*a*);
b) Forming a malleable layer of a hydrophilic and porous material (3) on said semipermeable membrane to form a composite matrix (3*b*);
c) Pressing a die (4) comprising a plurality of tapered protuberances (4*a*) into an outer surface (3*b*) of the malleable layer of hydrophilic and porous material of said composite matrix (3*b*) to form a plurality of well-shaped indents in said layer (5);
d) Removing the die (4) from layer of hydrophobic polymer to obtain an imprinted composite matrix (6) comprising a hydrophilic and porous material layer with a plurality of lasting well-shaped indents (5) on its outer surface supported by a semipermeable membrane on its inner surface (2).

According to a particular aspect, the support frame comprises a material that does not irreversibly adhere to the hydrophilic material such as polyethylene, polystyrene, polypropylene, polycarbonates and any organic hydrophobic plastics. The semipermeable membrane is attached to the support frame at its edges and can be in the form of a ring, a square or a rectangular frame surrounding the semipermeable membrane to impart a certain axial rigidity and planarity to the surface of the membrane.

According to a particular aspect, the semipermeable membrane allows air/liquid interface cell culture conditions. Typically, a semipermeable membrane according to the invention has pores having a diameter from about 1 nm to about 200 μm, for example from about 2 nm to about 40 μm.

According to another aspect, typically, a semipermeable membrane according to the invention has pores from about 0.4 μm to about 12 μm. According to another particular aspect, the semi-permeable membrane is a membrane comprising or consisting of at least one material selected from polytetrafluoroethylene, polycarbonate, polyethylene terephthalate and cellulose esters or a combination thereof.

According to another particular aspect, the semi-permeable membrane is a membrane comprising or consisting of at least one material selected from polystyrene sulfonate and polypropylene.

According to a further particular aspect, the hydrophilic and porous material is a hydrophilic gel allowing the diffusion of aqueous cell culture medium and not attaching to cells. Typically, a hydrophilic gel according to the invention is made from a polymer selected from agarose, Polyvinyl (alcohol) (PVA), agar-agar, alginates, hyaluronic acid, pectin or starch or any equivalent synthetic gel.

According to another further particular aspect, a hydrophilic gel according to the invention is made from a polymer selected from cell compatible naturally (or modified) derived materials selected from carbohydrates (e.g. agarose, agar-agar, alginate, starch, pectin, chitosan, dextran, polysachrides), proteins or ECM components (e.g. laminins, collagens, hyaluronan, fibrin), peptides (e.g. gelatin), and mixtures thereof; or a gel derived from natural ECM, preferably Matrigel™ (a reconstituted basement membrane preparation that is extracted from mouse sarcoma, a tumor rich in extracellular matrix proteins (this material, once isolated, contains approximately 60% laminin, 30% collagen IV, and 8% entactin. Entactin is a bridging molecule that interacts with laminin and collagen IV and contributes to the structural organization of these extracellular matrix molecules. Corning Matrigel™ matrix also contains heparan sulfate proteoglycan (perlecan), transforming growth factor (TGF-beta), epidermal growth factor (EGF), insulin-like growth factor (IGF-1), fibroblast growth factor (bFGF), tissue plasminogen activator, and other growth factors which occur naturally in the EHS tumor. There are also residual matrix metalloproteinases derived from the tumor cells), Myogel (a human-based extracellular matrix myogel is extracted from human benign tumor tissue "leiomyoma" as described in Abberton et al., 2008, Cells Tissues Organs, 188 (4): 347-58. doi: 10.1159/000121575. Epub 2008 Mar. 20. PMID: 18354248; Salo, et al., 2015, BMC Cancer, 15, 981 doi.org/10.1186/s12885-015-1944-z, or Cartigel (an extracellular matrix extract of cartilage) or synthetic derived materials selected from poly(ethylene glycol), polyaliphatic polyurethanes, polyether polyurethanes, polyethylene copolymers, polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxy ethyl acrylate), poly (hydroxyethyl methacrylate), and mixtures thereof.

According to a further particular aspect, the hydrophilic gel can be prepared by many methods known in the art and involve covalent crosslinking or non-covalent assembly, or a combination of both. Covalent crosslinking can further be carried out as part of the synthesis process, for instance by using bifunctional monomers during polymerization, or alternatively by crosslinking of pre-formed macromolecules of hydrophilic polymers, wherein the polymers are linear or branched, using natural or synthetic macromolecules in the process.

According to a further particular aspect, a malleable layer of a hydrophilic and porous material is a layer of a hydrophilic gel formed at a temperature above the gelling temperature of the gel (e.g. from 20° C. to 100° C. above the said gelling temperature). Typically, a malleable layer of agarose is formed by depositing agarose at a temperature between 75° C. and 100° C. on the semipermeable membrane to form a composite matrix.

According to a further particular aspect, a malleable layer of a hydrophilic gel is from about 5 mm to 10 cm large and from about 2 mm to 10 mm thick when above the gelling temperature. Hydrophilic gels advantageously prevent adhesion of cells and of spheroids, once formed, thereby avoiding the use of an anti-adherent solution prior to centrifugation during cell culture.

According to a further particular aspect, a malleable layer of a hydrophilic and porous material according to the invention has a porosity which allows the passage of oxygen and cell nutrients. Typically, its porosity ranges from about 10 nm to about 500 μm.

According to a further particular aspect, a malleable layer of a hydrophilic and porous material according to the invention such as agarose has a porosity range from about 100 nm to about 500 mm mostly occupied by water molecules, allowing the passage of nutrients, small molecules, chemical compounds and even proteins such as albumin.

According to a particular embodiment, the die comprises a handle and a patterning surface, said patterning surface having a size from about 1 $mm^2$ to 2,000 $cm^2$, for example from about 1 $mm^2$ to 100 $cm^2$, being made from a moldable hydrophobic material and comprising a plurality of tapered protuberances (e.g. of triangular or linear or ovoidal pyramidal or circular shape), wherein said tapered protuberances have base surface area from about 100 μm$^2$ to 10 cm$^2$, for example from 100 μm$^2$ to 1 mm$^2$ and a tip surface area from about 0 μm$^2$ to about 1 mm$^2$, for example from about 100 μm$^2$ to 1 mm$^2$.

According to a particular embodiment, the die comprising a plurality of tapered protuberances is pressed into an outer surface of the malleable layer of hydrophilic and porous material of said composite matrix such that the protuberances penetrate into the malleable layer of hydrophilic and porous material until the upper extremity of protuberances is in contact with the semipermeable membrane.

According to a particular aspect, the die is removed from the hydrophilic material to obtain an imprinted composite matrix, once the temperature of the hydrophilic gel is lower than its gelling temperature.

According to a particular aspect, the imprinted composite matrix comprises a hydrophilic and porous material layer with a plurality of lasting well-shaped indents on its outer surface supported by a semipermeable membrane on its inner surface, wherein the well-shaped indents have an aperture from about 100 μm$^2$ to 10 cm$^2$, for example from about 100 μm$^2$ to 1 mm$^2$, a depth from about 100 μm to 40 mm, for example from 100 μm to 1 mm and a bottom surface area from about 0 μm$^2$ to 1 mm$^2$, for example from about 100 μm$^2$ to 1 mm$^2$. According to particular aspect, well-shaped indents in the form of pyramide, a suitable bottom: aperture ratio of those wells can be about 0.8:3.

According to a particular aspect, the imprinted composite matrix comprises a hydrophilic gel layer with a plurality of lasting well-shaped indents on its outer surface supported by a semipermeable membrane on its inner surface, wherein the density of the well-shaped indents on the surface of the layer of a hydrophilic gel is from about 10 cm$^{-2}$ to 10,000 cm$^{-2}$.

According to a particular aspect, well-shaped indents are inversed pyramidal cavities (<1 mm).

According to a further particular aspect, a method for preparation of a substrate material for cell culture according to the invention is suitable for the culture of spheroids.

According to another further particular aspect, the well-shaped cavities on the surface of the layer of a hydrophilic material allows focal clusterization of cells at their bottom upon gravity during cell culture or centrifugation.

According to another further particular aspect, the imprinted composite matrix comprises a hydrophilic gel layer with a plurality of lasting well-shaped indents on its outer surface supported by a semipermeable membrane on its inner surface is particularly suitable for air/liquid interface cell culture conditions. In particular, the hydrophilic and porous nature of the hydrophilic gel (e.g. agarose) allows diffusion of culture medium located under the semipermeable membrane, to create a film of culture medium on the cells and formed spheroids.

According to another further particular aspect, the obtained imprinted composite matrix can be readily used after its formation or can be stored for a later use. For example, the imprinted composite matrix can be stored within a buffer solution at 4° C. or at room temperature or in frozen state or in a closed container in absence of buffer, preferably under vacuum or in lyophilized form.

According to a further particular aspect, the method according to the invention may further comprise a step of preparing the obtained composite matrix for storage (e.g. for example at least one steps selected from conditioning the composite matrix in a sealed container under vacuum, lyophilizing or freezing the composite matrix).

Dies Suitable for the Preparation of a Substrate Material According to the Invention Referring to the figures, in particular to FIGS. 2A-B and 2E-F, is provided a die for the preparation of a substrate material for cell culture, said die (44) comprises a handle (45) and a patterning surface (46), said patterning surface having a size from about 1 mm$^2$ to 100 cm$^2$, being made from a moldable hydrophobic material and comprising a plurality of tapered protuberances (44*a*) (e.g. of triangular or linear or ovoidal pyramidal shape), wherein said tapered protuberances have base surface area (44*b*) from 100 μm$^2$ to 1 mm$^2$ and a tip surface area from 100 μm$^2$ to 1 mm$^2$.

According to a particular embodiment, a moldable hydrophobic material is selected from silicones, (Meth)acrylate-based photocurable systems, Thiol-ene and Thiol-yne photocurable systems, Epoxy or Bisphenol-F epoxy resins, Polyester, epoxy and polyurethane, Bisphenol type epoxy, ABS and reinforced ABS (Acrylonitrile Butadiene styrene), PMMA-ABS (Polymethyl methacrylate ABS), SEBS-ABS (Styrene-ethylene-butadiene-styrene/ABS), UHMWPE-ABS (ultrahigh molecular wight polyethylene-ABS), PLA-PBS (polylactic acid-polybutylene succinate)), TPU (polyurethane), PLA (polylactic acid), PVA (polyvinyl alcohol), PET-PEPN (polyethylene terephtalate-phenylacetylene), PIB (polyisobutylene), PTFE (polytetrafluoroethylene, PDMS (polydimethylsiloxane), PC (polycarbonate), PPS (polyphenylsulphone) and PEI (polyetherimide).

According to another particular embodiment, a moldable hydrophobic material is stainless steel.

According to another particular embodiment, a moldable hydrophobic material is selected from dioxide and nitrate silicones.

According to a particular aspect, a die according to the invention can be prepared by molding a hydrophobic material such as polydimethylsiloxane (PDMS) in suitable a female mold comprising well-shaped cavities of 1 μm$^2$ to 1 mm$^2$ (e.g. Aggrewells™ wells) or by 3D printing by using UV curable methacrylate resins on a SLA (Stereolithography) or a DLP (digital light processing) 3D-printer. The advantage of 3D printing is the possibility to create any design of any tapered protuberances in terms of their size, depth and shape.

Substrate Material According to the Invention Useful for the Formation of Spheroids According to a particular embodiment, is provided a substrate material obtainable from a method according to the invention.

Referring to the figures, in particular to FIGS. 3A and B, is provided a substrate material (6) for the preparation of spheroids wherein said material comprises: a hydrophilic and porous material layer (3) with a plurality of lasting well-shaped indents (5) on its outer surface supported by a semipermeable membrane (2) on its inner surface and wherein the semi-permeable membrane is supported by a support frame (2*a*) on its edge wherein said well-shaped indents have an aperture from 1 μm$^2$ to 1 mm$^2$ and a bottom surface from about 1 μm$^2$ to 1 mm$^2$.

According to a particular aspect, the hydrophilic and porous material layer is a hydrophilic gel layer, for example from agarose, polyvinyl(alcohol) (PVA), agar-agar, alginates, hyaluronic acid, pectin, starch or any synthetic hydrogel which do not attach to cells.

According to another particular aspect, is provided a substrate material for the preparation of spheroids according to the invention, said substrate material comprising a hydrophilic material layer with a plurality of lasting well-shaped indents on its outer surface supported by a semipermeable membrane on its inner surface and wherein said well-shaped indents have an aperture from 100 μm$^2$ to about 1 mm$^2$ and a bottom surface from about 100 μm$^2$ to about 1 mm$^2$.

According to another particular aspect, is provided a substrate material for the preparation of spheroids according to the invention comprising an imprinted composite matrix according to the invention.

According to another particular aspect, is provided a substrate material for the preparation of spheroids according to the invention, wherein said plurality of lasting well-shaped indents is between 4 to 1'536 well-shaped indents.

According to another particular aspect, the semi-permeable membrane is as described herein.

According to another aspect, the substrate material of the invention is in frozen state, e.g. for storage or transport.

According to another further aspect, the substrate material of the invention further comprising an individualized spheroid or individualized organoid in each of the well-shaped is in frozen state, e.g. for storage or transport.

For a further use, the frozen substrate material of the invention can then be either cryosectioned or thawed, for example by freezing well-shaped indents of substrate material of the invention containing the formed spheroids directly in Milestone Cryoembedding Compound (MCC) and then cut with a cryostat to thicknesses ranging from 5 μm to 20 μm as described in the example 6. The sections are then collected on slides before being visualized under a microscope.

According to a particular aspect, a substrate material according to the invention is useful for the preparation of spheroids or organoids, in particular in a method according to the invention.

According to a particular aspect, a substrate material according to the invention is useful for the preparation of spheroids or organoids for research purposes.

According to another particular aspect, a substrate material according to the invention is useful for the preparation of spheroids or organoids for clinical and cell therapy purposes.

Method of Preparation of Spheroids According to the Invention

Referring to the figures, in particular to FIGS. 3A and B, is provided a method for the preparation of spheroids, said method comprising the following steps:

i) Providing a spheroid culture medium (8) in a cell culture vessel (7);

ii) Placing a substrate material (6) comprising a hydrophilic and porous material layer (3) with a plurality of lasting well-shaped indents (5) on its outer surface supported by a semipermeable membrane on its inner surface (2) and wherein the semi-permeable membrane is supported by a support frame (2*a*) on its edge on the surface of the culture medium such that the substrate material is floating on the surface of a culture medium;

iii) Contacting a cell suspension (9) with the surface of the floating substrate material until cells forms spheroids on the surface of the floating substrate material.

According to a particular aspect, the volume of spheroid culture medium is from about 1 μl to about 1,000 ml.

According to another particular aspect, a cell suspension according to the invention is prepared by mixing cells with a cell compatible material that favors spheroid/organoid cell culture (e.g. differentiation, proliferation or maintenance), such cell compatible material comprises naturally derived biomaterials such as polysaccharides, gelatinous proteins, Extracellular matrix (ECM) components comprising: agarose; alginate; chitosan; dextran; gelatin; laminins; collagens; hyaluronan; fibrin, functional variants, and mixtures, or a gel derived from natural ECM, as Matrigel™, Myogel or Cartigel.

According to another particular aspect, the formation of spheroids can be achieved under step iii) over time by gravity from about 2 h to 5 h or by subjecting the cell culture vessel containing the cell seeded floating substrate material to centrifugation to induce cell aggregation.

According to a particular aspect, the cell culture vessel is centrifuged at 100×g for a period from 5 to 10 minutes.

According to a particular aspect, the cells are stem cells such as pluripotent stem cells, adult stem cells, induced pluripotent stem cells, mesenchymal stem cells.

According to a particular aspect, the cell suspension is an ASC suspension. According to a particular embodiment, ASC are detached by enzymatic treatment (trypsin/EDTA or TrypLE) before preparing a cell suspension.

According to a particular aspect, the cell suspension is a dopaminergic neural cell suspension.

According to a particular aspect, the cell suspension is non-human embryonic stem cell suspension.

According to a particular aspect, the cell suspension is pluripotent stem cell suspension.

According to a particular aspect, the cells are used in a method of the invention in co-culture. In particular, the cell are provided as a mixture of two or more of following cell types: fibroblasts, endothelial cells, immune cells, muscle cells, blood cells, vascular cells, multipotent stem cells, unipotent stem cells, Mesenchymal Stem Cells, Adipose-derived Stem Cells, hepatocytes, cardiomyocytes, chondrocytes, neural cells, neurons, astrocytes, oligodendrocytes, pluripotent stem cells, iPS, embryoid bodies, skin cells, lung epithelial cells, all tumor cells, hepatic cells, pancreatic cells, intestinal cells, epidermal cells, keratinocytes or bone cells and in general adherent cells (stem cell or not such as), non-adherent cells or mixture.

According to a further particular embodiment, co-culture can be carried out by directly using the co-culture as the cell suspension contacting the surface of the floating substrate material until cells forms spheroids on the surface of the floating substrate material.

Alternatively, co-culture can be carried out by cultivating other cell types in the culture medium on which the substrate material is floating (e.g. in the basal part of the vessel containing the culture medium).

According to another particular aspect, the cell co-culture comprises the combination of fibroblasts and cancer cells.

According to another particular aspect, the cell co-culture comprises the combination of fibroblasts and hematopoietic cells.

According to another particular aspect, the cell co-culture comprises the combination of neuronal cells and vascular cells.

According to another particular aspect, the cell co-culture comprises the combination of neural cells and immune cells.

According to another particular aspect, the cell co-culture comprises the combination of cancer cells and immune cells.

According to another particular aspect, the cell co-culture comprises the combination of liver cells and immune cells.

According to a particular aspect of the invention, the spheroids obtained by a method of the invention may be used readily (e.g. for use as a cell material useful in regenerative or replacement therapies or as substrate for in vitro assays as described in the Examples or for the formation of organoids), by isolating them from the substrate such as by pipetting.

Alternatively, the spheroids obtained by a method of the invention may maintained in culture for example for preparing organoids and in this case, the formed spheroids are maintained on the surface of the floating substrate material until maturation or differentiation while regularly changing the culture medium under the substrate material (e.g. every 2-3 day).

According to a particular aspect, a method for the preparation of spheroids according to the invention is carried out under air-liquid interface conditions and presents several advantages: (i) changes of culture media can be made on the side of the substrate which is not in contact with the spheroids (on the side of the semi-permeable membrane in contact with the culture medium) thereby avoiding destabilization of spheroids that might prevent fusion; (ii) spheroids are individualized during their formation within the well-shaped indents and stabilized individually by the formation of a film of culture medium on the formed spheroids, the combination of well-shaped indents and film formation preventing the migration of spheroids and their fusions; (iii) exchanges between the cells and air prevent the formation of hypoxic and necrotic cores in spheroids that are present under these static culture conditions.

According to a particular aspect, a method according to the invention advantageously allows the preparation of spheroids with a very high homogeneity of the obtained spheroids (size & shape) which are stable over time at least 6 weeks.

According to a particular aspect, a method according to the invention advantageously allows the preparation of spheroids with a very high homogeneity of the obtained spheroids (size & shape) which are stable over time at least 5 months. Indeed, at 5 months the diameter of the spheroids has a standard deviation of 81 μm in comparison to 563 μm for the spheroids cultivated with the classical method. Moreover, concerning the analysis of the shape of the spheroids, the evaluation of the roundness whose ratio is equal to 1 for a perfect circle, the spheroids produced by the method of invention has a roundness of 0.92+/−0.02 against 0.85 +/−0.05 for the spheroids cultivated by the traditional method in immersion.

This method further allows the reduction of manufacture time and costs thereby reducing the quantity of medium required and intervention.

This method allows an easy change of culture medium without inducing microfluidic perturbations on the formed spheroids once the spheroids are maintained in culture for a certain time (e.g. for the formation of organoids).

This method further prevents the formation of a necrotic core and fusions between spheroids. Finally, the formation of the spheroids can be easily observed under inversed microscopy.

Spheroids According to the Invention and Uses Thereof

According to a particular embodiment, is provided spheroids obtainable from a method according to the invention.

According to a particular embodiment, is provided individualized cell spheroid essentially free from necrotic cores and stable for at least 6 weeks, for example for at least 5 months.

According to a particular embodiment, is provided individualized cell spheroid of the invention wherein hypoxia-related genes such as LDHA, EGFR, VEGFC are not upregulated as compared to the spheroids cultivated by the classical method in immersion and under rotation.

The method according to the invention is very advantageous since the formation of ASC spheroids for clinical applications has not been achieved before.

According to another aspect of the invention, is provided ASC spheroids, in particular individualized ASC spheroids having homogeneous characteristics (size & shape) and long-term stable properties with a gene expression profile that differ from ASC spheroids obtained by any other known methods. In particular, those ASC spheroids have an expression profile where extracellular matrix proteins are highly expressed.

According to another aspect of the invention, is provided neurospheres, in particular individualized neurospheres having advantages over neurospheres prepared by known methods. In particular, the invention provides individualized neurospheres with homogeneous characteristics (size & shape) and long-term stable properties with a gene expression profile with an increased neural progenitor cells gene expression.

According to another aspect of the invention, is provided spheroids according to the invention for use in regenerative medicine such as fat transplantation, in particular for the treatment of and skin wounds and in cell therapy for autologous fat transplantation (e.g. using ASC spheroids), bone and cartilage repair (e.g. using ASC, chondrocyte or osteocyte spheroids), skin repair (e.g. using keratinocyte or fibroblast spheroids), heart tissue repair (e.g. using cardiomyocyte spheroids), notably useful in the treatment of cardiac ischemia, pancreatic cells transplantation (e.g. using Langherans islets spheroids) notably useful in diabetes or in the treatment of neuronal damage (e.g. using neurospheres) such as in the treatment of stroke, traumatic brain injury, neurodegenerative disorders such as Parkinson's disease.

According to another aspect of the invention, is provided the use of ASC spheroids for the preparation of cell tissues useful for the treatment of chronic wounds.

According to another aspect of the invention, is provided a tissue substitute comprising ASC spheroids according to the invention, for example in the form of a hydrogel comprising alginates, chitosan, collagens, hyaluronic acid, glycosaminoglycans, pectin, carboxymethylcellulose, polyvinylpyrrolidone further comprising ASC spheroids according to the invention.

According to another aspect of the invention, is provided a pharmaceutical or cosmetic composition comprising ASC spheroids according to the invention and at least one pharmaceutically or cosmetically acceptable carrier. Example of those compositions can be ointments, pomades or creams for topical uses.

According to another aspect of the invention, is provided the use of neurospheres for the preparation of cellular substitutes useful for neural tissue modelization or in drug screening and toxicity assays or cell replacement therapy.

According to another aspect of the invention, is provided a cellular or tissue substitute comprising neurospheres according to the invention, such as described in Campos et al., 2004, *J. Neurosci. Res.,* 1578(6): 761-9; Takahashi, 2006, *J. Ernst Schering Res. Found. Workshop.,* (60): 229-44; Gottlieb, 2002, *Annu Rev Neurosci.,* 25:381-407.

According to another aspect of the invention, is provided a method for the regeneration of a biological tissue, said method comprising contacting one or more individualized cell spheroids according to the invention with said biological tissue. In particular, is provided an ex-vivo method for the regeneration of a biological tissue wherein said one or more individualized cell spheroids is used to prepare ex-vivo a cell tissue useful for tissue regenerative or tissue replacement therapy.

According to another aspect of the invention, the spheroids according to the invention can be used for humanization of mice: a humanized mouse is an immunodeficient laboratory mouse that either expresses a human gene or has been transplanted with human stem cells or tissue. In this context, spheroids or organoids replicating organs such as brain, liver or pancreas produced by the method of the invention can be grafted into these types of mice to humanize them.

Kits According to the Invention

According to another aspect of the invention, is provided a kit for the preparation of a substrate material allowing the preparation of spheroids in an efficient, accurate and reliable manner, said kit comprising at least one die according to the invention and instructions for use.

According to another aspect of the invention, is provided a kit for the preparation of a substrate material for the preparation of spheroids further comprising at least one of the further elements:

- A hydrophilic and porous material useful for the formation of a hydrophilic gel, e.g. selected from agarose, polyvinyl(alcohol) (PVA), agar-agar, alginates, hyaluronic acid, pectin or starch or any equivalent synthetic gel;
- A semi-permeable membrane, e.g. a membrane comprising or consisting of at least one material selected from polytetrafluoroethylene, polycarbonate, polyethylene terephthalate and cellulose esters or a combination thereof alone or removably seated on a support base.

According to another aspect, a semi-permeable membrane according to the invention comprises or consists of at least one material selected from polystyrene sulfonate and polypropylene.

According to another aspect of the invention, is provided a kit for the preparation of spheroids, said kit comprising at least one substrate material according to the invention and instructions for use.

According to another particular aspect, is provided a kit for the preparation of spheroids, said kit comprising at least one substrate material according to the invention, wherein said substrate material comprising a plurality of well-shaped indents from 4 to 1,536 well-shaped indents.

According to another aspect of the invention, is provided a kit for the preparation of spheroids further comprising at least one of the further elements:

- A cell culture medium;
- A cell culture vessel;
- A tool for handling the substrate material according to the invention.

According to another aspect of the invention, is provided a kit according to the invention wherein a cell culture vessel is a cell culture dish having a surface from between about 25 $cm^2$ up to 1,720 $cm^2$.

According to another aspect of the invention, is provided a 3D in vitro culture system kit, said kit comprising at least one substrate material according to the invention, wherein said substrate material further comprises an individualized spheroid or individualized organoid in each of the well-shaped indents, a cell culture medium suitable for supporting spheroids organoid maintenance and instructions for use.

According to another aspect of the invention, is provided a 3D in vitro culture system kit, said kit comprising:

- a substrate material comprising a hydrophilic and porous material layer with a plurality of lasting well-shaped indents on its outer surface supported by a semipermeable membrane on its inner surface and wherein the semi-permeable membrane is supported by a support frame on its edge, wherein the said substrate material comprises an individualized spheroid or individualized organoid in each of the well-shaped indents;
- a cell culture medium suitable for supporting spheroids organoid maintenance;
- wherein said substrate material is floating on the surface of the said culture medium; and instructions for use.

According to another aspect, is provided a 3D in vitro culture system kit wherein said substrate material comprising an individualized spheroid or individualized organoid in each of the well-shaped indents is frozen.

According to another aspect, is provided a 3D in vitro culture system kit wherein said substrate material comprising an individualized spheroid or individualized organoid in each of the well-shaped indents is frozen in slices from about 5 to about 20 μm thickness. The slices can be obtained by cryosection with a cryostat.

According to another further aspect, is provided a 3D in vitro culture system kit, wherein said substrate material is provided in a cell culture vessel, preferably with a lid.

According to another further aspect, the cell culture vessel and the lid are made in a transparent material (e.g. polystyrene, glass or plates with thin polystyrene film or coverglass bottoms).

According to another aspect of the invention, is provided a cell culture system comprising a plurality of cell culture vessels, each cell culture vessel comprising a substrate material according to the invention wherein said substrate material is floating on the surface of a cell culture medium. Typically, the cell culture vessel surface of the said plurality of cell culture vessel represents a surface from about 0.011 $cm^2$à 500 $cm^2$. Typically, the medium volume of the culture medium is from about 1 μl to about 150 ml.

According to another aspect of the invention, is provided a kit or a cell culture system according to the invention wherein said kit or system is useful to generate cerebral, liver, lung, adipose-Derived-Stromal cells spheroids or cancer organoids.

According to another aspect of the invention, is provided a kit or a cell culture system according to the invention wherein said kit or system is useful to preserve the stability and integrity of spheroids organoids and conveniently transport them without structural alteration.

According to another aspect of the invention, is provided a kit or a cell culture system according to the invention wherein said kit or system is useful to carry out frozen sections/cryosections of several spheroids/organoids in the same plane and to carry out the various histological or immunohistochemical markings in succession. Frozen section technique shortens the time to preliminary histological analyses significantly from traditional tissue biopsy preparation, allow a high accuracy and preserves enzyme & antigen function.

Examples illustrating the invention will be described hereinafter in a more detailed manner and by reference to the embodiments represented in the Figures.

EXAMPLES

The following abbreviations refer respectively to the definitions below:

Example 1: Preparation of a Substrate Material of the Invention

A method for the preparation of a substrate material of the invention useful for the preparation of spheroids which is illustrated on FIG. 1A was carried out. In particular, the method comprised the following steps:

a) Providing a semipermeable membrane (2) supported by a support frame on its edges (2*a*)

A semi-permeable membrane of polycarbonate supported by a support frame of polystyrene is provided (Millicell Cell Culture Insert, 30 mm, polytetrafluoroethylene, pores of 0.4 μm).

b) Forming a malleable layer of a hydrophilic and porous material in the form of hydrophilic gel (3) on said semipermeable membrane to form a composite matrix (3*a*)

1 ml of heated agarose (100° C.) (LE, Analytical Grade, Promega) at 2.5% in ultrapure water (1) was formed on the supported semi-permeable membrane described before, thereby forming a composite matrix (3*a*) comprising a malleable layer (1 mm) of agarose (3) on the semipermeable membrane.

c) Pressing a die (4) comprising a plurality of tapered protuberances (4*a*) into an outer surface (3*b*) of the malleable layer of hydrophilic and porous material of said composite matrix (3*a*) to form a plurality of well-shaped indents (5) in said layer A die (4) comprising plurality of pyramidal protuberances (4*a*) as described below was then immediately pressed into the outer surface of the heated agarose layer before agarose jellification such that protuberances are in contact with the semipermeable membrane to form a plurality of well-shaped indents (5) on the agarose layer surface (3).

Figure 1B:
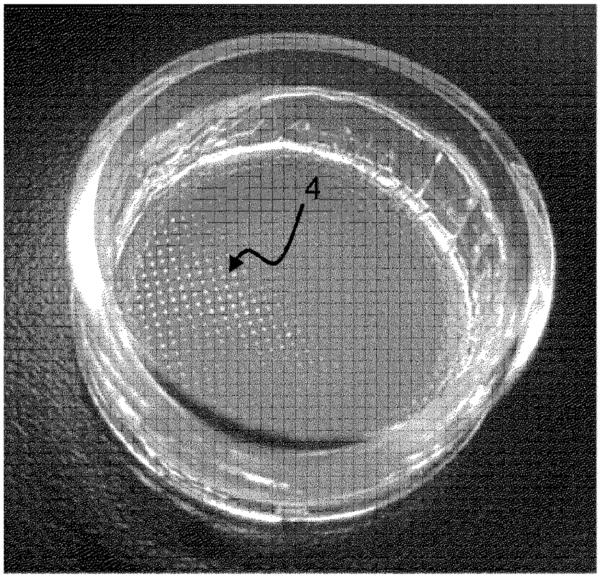
Figure 1C:
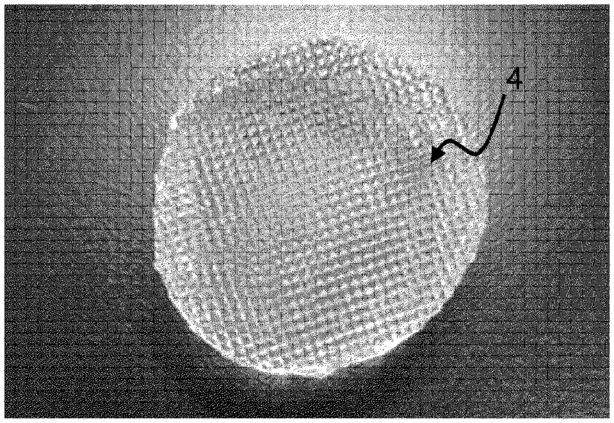
Figure 2:
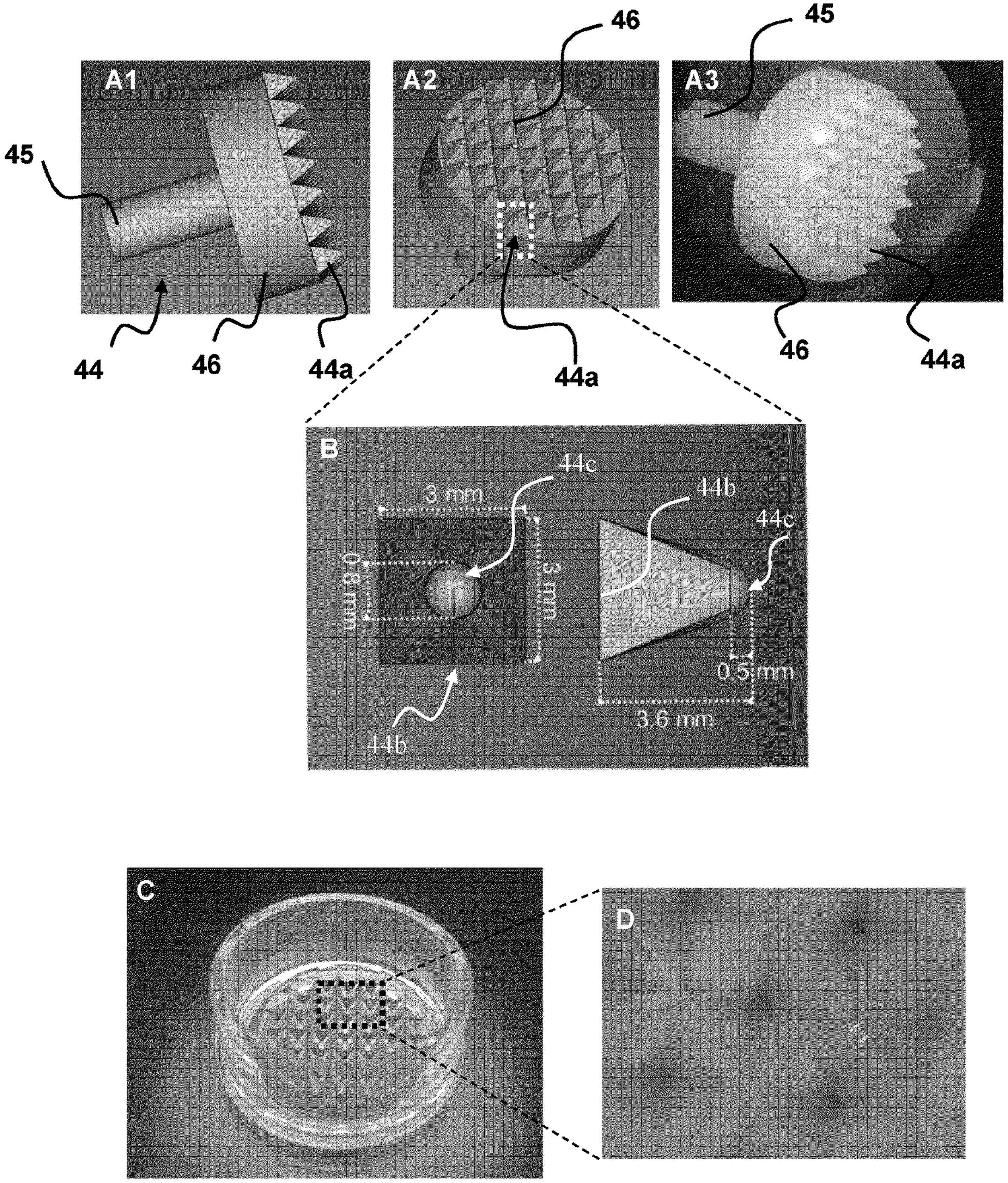
FIG. 2 shows various examples of dies useful for preparing a substrate material according to the invention (37 protuberances of 3×3×3.6 mm for A1-A3 and 373 protuberances of 1×1×1.16 mm for E1-E3, A1-A2 and E1-E2 being designed die and A3 and E3 being the manufactured die), a detail of tampered protuberances for the exemplified die (B and F, respectively), the corresponding supported agarose layer comprising a plurality of well-shaped indents resulting from step c) (C and G, respectively) and a microscopic view of the well-shaped indents in an agarose layer (D and H, respectively).
Figure 2:
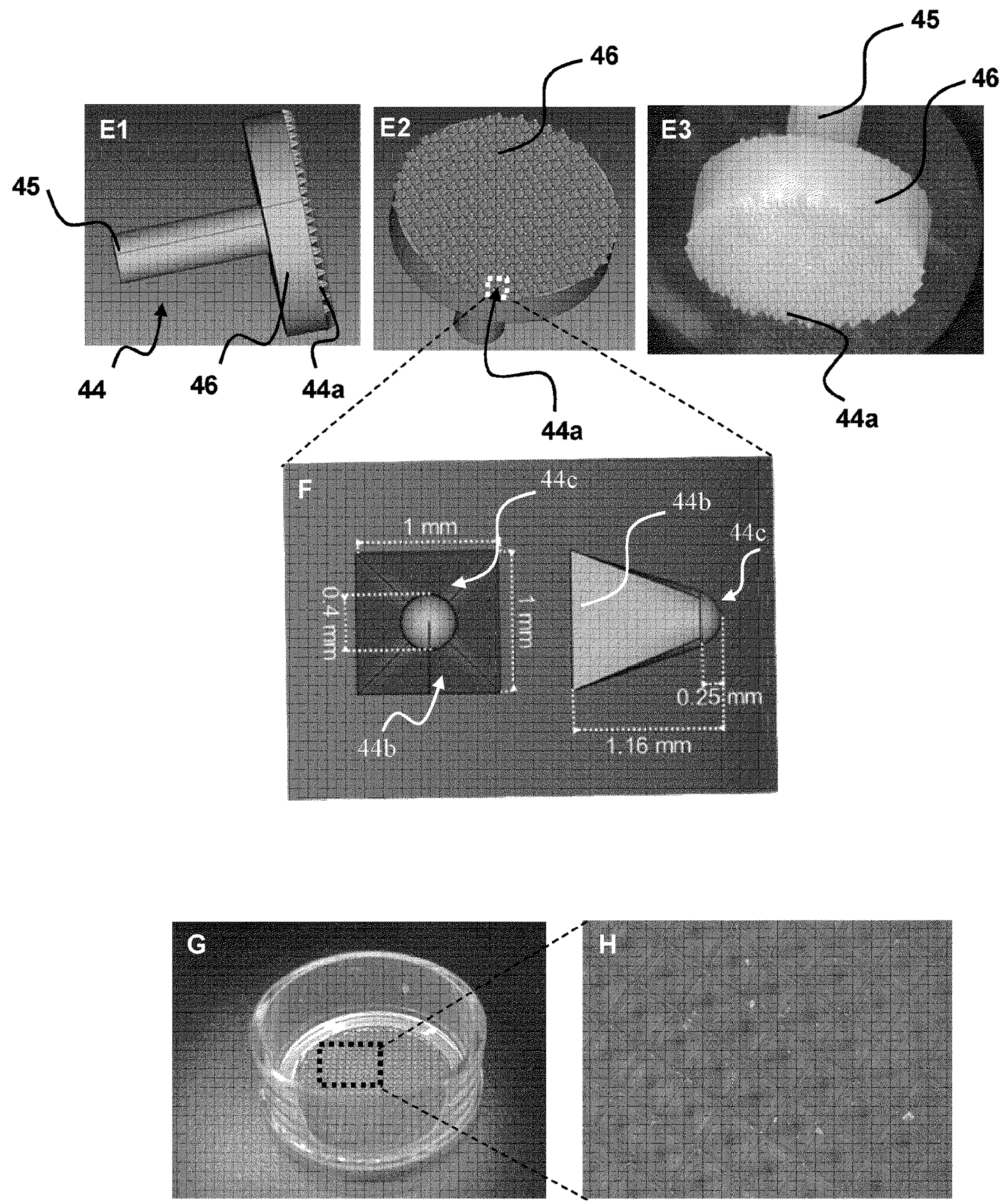

Dies used were made in silicon and prepared with a silicon elastomer kit (polydimethylsiloxane (PDMS), SYLGARD 184, RTV, Dow Corning, United States) used according to the manufacturer's protocol. For this, the Sylgard 184 polymer and the curing agent were mixed at the prescribed ratio of 10:1, degassed for 30 minutes under vacuum, and poured into a microwell culture plate (Aggrewell™ plate) (FIG. 1B), thereby forming a silicon dye die comprising plurality of protuberances (FIG. 1C) of the size and form of the microwell culture plate.

Alternatively, 3D-printed dies were designed with a parametric 3D modeler (e.g. FreeCAD 0.18). Then, the generated designs were exported as STL format files and transduced into a G-code (e.g. Autodesk Netfab2020 software) and the resulting file was imported into a digital light processing (DLP) 3D printer (Rapidshape P30 series, Straumann®) with a UV 385 nm high power led and a HD resolution of 1920×1080px. An acrylic resin (Sheraprint model plus sand UV) was used to print the die with a layer thickness of 50 μm. Once printed, the models were washed two times for 6 min in isopropanol in an ultrasonic bath (28-34 kHz) at room temperature. Once dried, the models were further cured in a curing unit (Shera flashlight-+3D): 2 cycles of 2000 flashes (100 W/280-700 nm/10 flashes per sec) before sterilization and use. Examples of dies for creating well-shaped indents are presented under FIG. 2: designed (A1 -A2) and manufactured (A3) for creating large well-shaped indents in the hydrophilic and porous material layer, such as in a supported agarose layer with large microwells (C-D); designed (E1-E2) and manufactured (E3) for creating small well-shaped indents in the hydrophilic and porous material layer such as in a supported agarose layer with microwells small microwells (G, H).

d) Removing the die (4) from layer of hydrophilic and porous material to obtain an imprinted composite matrix (6) comprising a hydrophilic and porous material layer with a plurality of lasting well-shaped indents on its outer surface (5) supported by a semipermeable membrane on its inner surface, said membrane being supported by a support frame at its edges After 10 minutes at room temperature, the die is gently removed and well-shaped indents in the agarose layer established (FIG. 1A, a)).

Figure 3:
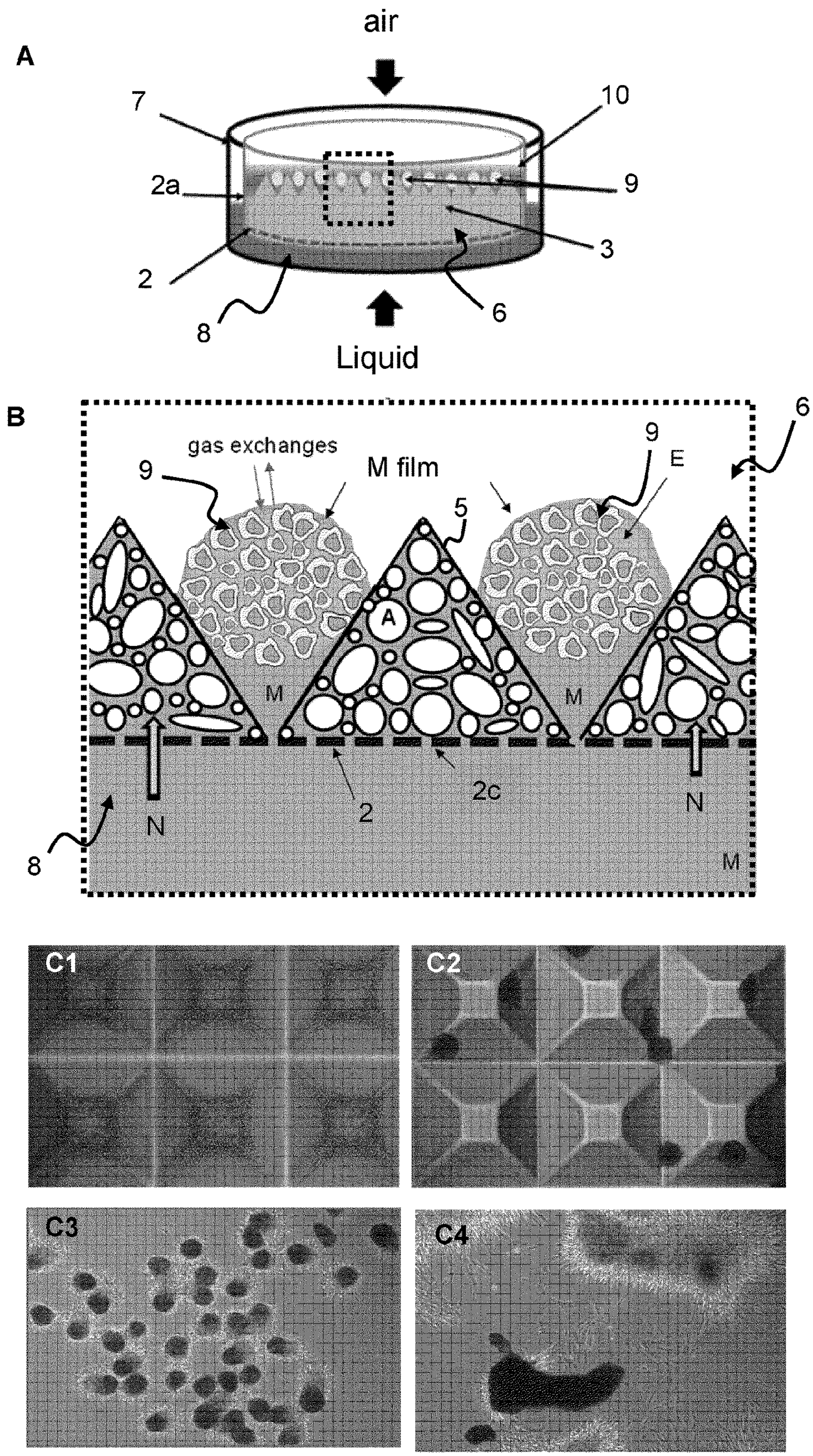
FIG. 3 provides an illustration the use of a substrate material according to the invention for the preparation of spheroids in a method according to the invention (A), a schematic representation of the formation of spheroids (surrounded by an extracellular matrix E) within the well-shaped indents in the substrate material according to the invention floating on a cell culture medium M (B) and a comparison by microscopy of the spheroids obtained by forced aggregation (C1-C4) and by a method according to the invention (D1-D3) as described in Example 2. Spheroid formation by a standard method of forced aggregation of an ASC cell suspension in Aggrewell™-800 (StemCell) microplates (comparative examples): C1: immediately after centrifugation; C2: 24 h after centrifugation of the plate; C3: Attachment to plastic of ASC spheroids 24 h after the transfer in cell culture plates 24 h after centrifugation of the plate; C4: Fusion and attachment to plastic of ASC spheroids 24 h after the transfer in cell culture plates and cultured under constant agitation 24 h after centrifugation of the plate. D1-D3: Spheroid formation by a method of the invention for 3 ASC lines (ASC9, ASC10, ASC11), 24 h after cell seeding.
Figure 3:
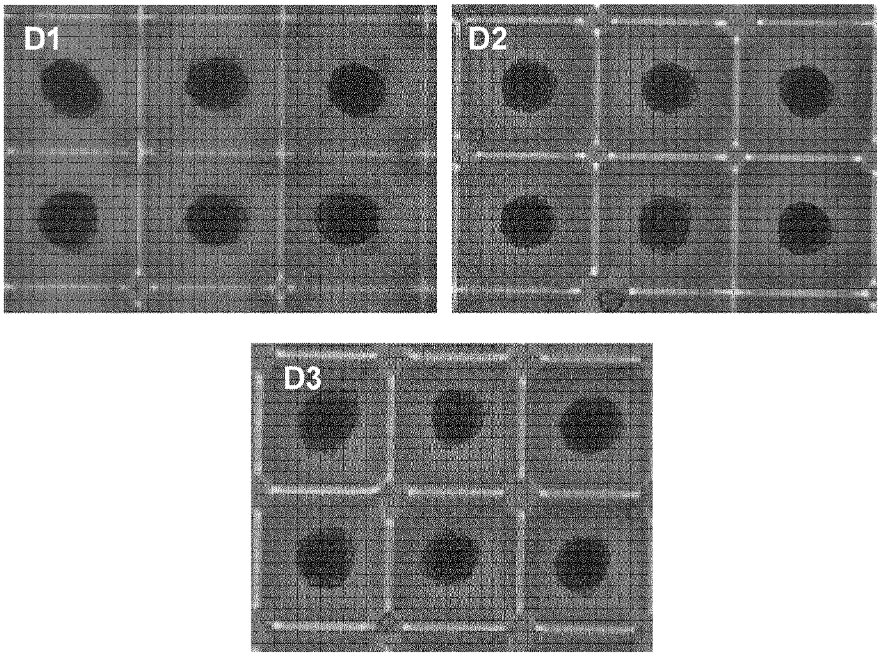

The resulting supported agarose layer comprising a plurality of well-shaped indents can then be used for the preparation of spheroids as described in Example 2 and FIG. 3. For example, it can be either stored, e.g. under vacuum or within a buffer or lyophilized or frozen for later use or immediately used for the preparation of spheroids.

Figure 4:
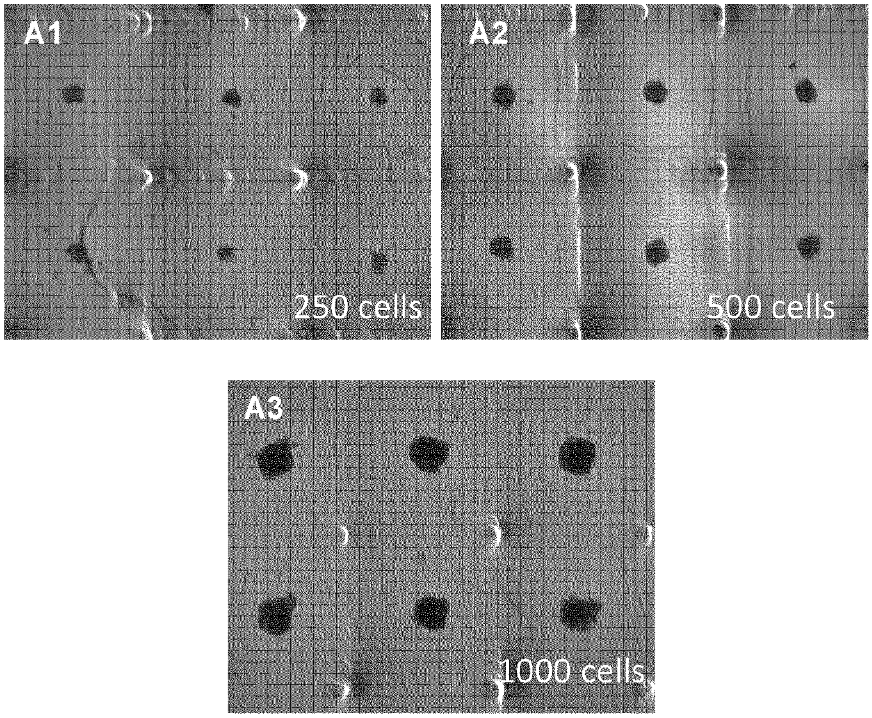
FIG. 4 shows pictures of the formation of different sizes of ASC spheroids using dies of FIG. 2, 24 h after contacting the cell suspension with the surface of the floating substrate material according to a method according of the invention. A1-A3: 3 different sizes of ASC spheroids obtained in small well-shaped indents in agarose using a die of FIG. 2E-F, typically ranging from 250 cells to 1000 cells; B1-B2: 2 different sizes of ASC spheroids obtained in large well-shaped indents in agarose using a die of FIG. 2A-B (typically ranging from 5000 cells to 10000 cells.
Figure 4:
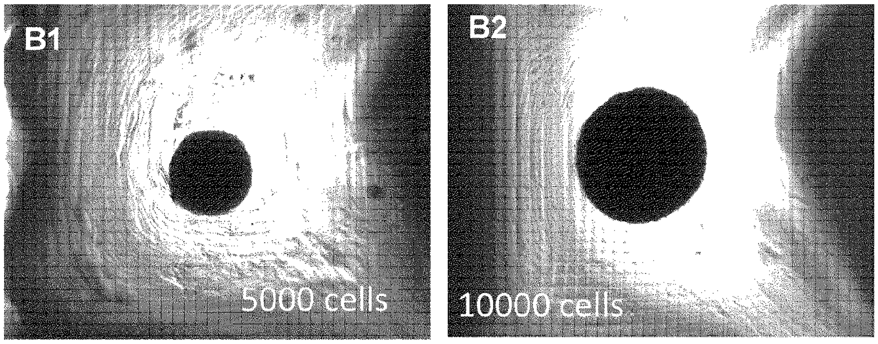

Supported hydrophilic gel layer with small indents were successfully used to produce different sizes of small ASC spheroids, ranging from 250 cells to 1,000 cells (FIG. 4A1-A3). Larger footprints were successfully used to produce different sizes of larger ASC spheroids, ranging from 5,000 cells to 10,000 cells (FIG. 43B1-B2).

Example 2: Manufacturing Adipose-Derived Stem Cells (ASC) Spheroids on a Substrate Material of the Invention The manufacturing of spheroids on a substrate of the invention was carried out from a culture of ASC and compared with the most standardized available method which is commercialized and based on forced aggregation, namely Aggrewell™ technology, as described in Mirab et al., 2019, *PLos ONE* 14(1):e0211078.

ASC Culture and Differentiation

ASC derived from human fat tissue surgical pieces (Ethical authorization NAC 14-183, Geneva University Hospitals, Dr Ilker Uckay) are grown in Dulbecco's Modified Eagle Medium (DMEM) (High glucose, L-Glutamine) culture medium supplemented with 10% of human platelet lysate (Stemulate, Cook Regentek), 1% penicillin and streptomycin antibiotics (all from Thermofisher). The cells are cultured at 37° C. and under 5% of $CO_2$. The medium is changed every 2-3 days, passaging done with 0.05% trypsin-EDTA solution (Thermofisher).

Known Method to Form ASC Spheroids (Aggrewell™ Technolog)

After forced centrifugation and 2 h of culture in a commercially available Aggrewell™-800 device, the cells clusterize (1,000 cells per spheroid, FIG. 3 C1) but after 24 h, the formed spheroids attached to the wells and moved outside the bottom of the wells (FIG. 3 C2) because ASC are also defined by their adherence to plastics used for cell culture (Bourin et al., 2013, *Cytotherapy,* 15(6):641-648). To solve this limitation, they must be transferred to a conventional 6-well plate to be cultured under agitation at 37° C., 5% $CO_2$. After transferring the spheroids into a conventional cell culture plate, the ASC spheroids rapidly adhere to the plastic (FIG. 3 C3) and also aggregate with each to merged into large aggregates (FIG. 3 C4), whose biological characteristics and therapeutic potential cannot be exploited.

ASC Spheroid Formation on a Substrate of the Invention i) Providing a spheroid culture medium in a cell culture vessel;

A culture medium (DMEM with 4.5 g/l of glucose and Glutamax (Thermofisher), penicillin and streptomycin 1%, 10% human platelet lysate (multiPL-100, Macopharma) suitable for the culture of spheroids derived from ASCs (8) is provided in a cell culture vessel such as a conventional 6-well plate (7) (FIG. 3A).

ii) Placing a substrate material (6) comprising a layer of hydrophilic and porous material with a plurality of lasting well-shaped indents on its outer surface (5) supported by a semipermeable membrane on its inner surface (2) on the surface of a culture medium such that the substrate material is floating on the surface of a culture medium A substrate material according to the invention in the form of a supported agarose layer comprising a plurality of well-shaped indents obtained in Example 1 (6) was deposited on the ASC culture medium M (8) to establish air/liquid interface conditions (FIG. 3A) in the cell culture vessel (7). A more detailed scheme of these air/liquid interface conditions is shown in (FIG. 3B) where the supported agarose layer comprising a plurality of well-shaped indents is floating on the culture medium.

iii) Contacting a cell suspension with the surface of the floating substrate material until the formation of spheroids An ASC single cell suspension (9) in their culture medium was filtered through a cell strainer (Corning, 40 μm) and 1 ml of suspension was deposited on the surface of the floating supported agarose layer comprising a plurality of well-shaped indents.

The cell culture vessel containing the cell seeded floating substrate material was subjected to centrifugation to induce cell aggregation: The 6-well plate was then centrifuged at 100× g for about 5 minutes to force aggregation of cells in the agarose wells. Medium is then removed by aspiration with a 0.5×16 mm needle and spheroids are just covered by a thin film (10) of residual medium. The hydrophilic properties of agarose and spheroids maintain by capillarity this thin film of medium, then creating air/liquid interface cell culture conditions.

Three ASC lines were first tested for the manufacturing of spheroids containing 1000 cells each, first by using a PDMS die to form a supported agarose substrate of the invention as described above. ASC spheroids after 24 h in air/liquid interface conditions did not attach to the agarose wells and harboured a round shape (FIG. 3, D1-D3). They were stable in these static conditions up to 6 weeks. The size of 30 spheroids inside 4 different ASC lines was measured using ImageJ™ software and the data were analysed as described below in Table 1.

TABLE 1

| ASC Line | ASC1 | ASC2 | ASC3 | ASC4 |
|---|---|---|---|---|
| Average diameter (μm, n = 30) | 166 +/− 5.3 | 168 +/− 4.3 | 159 +/− 5.2 | 172 +/− 4.5 |

For each of the lines, the standard deviation between spheroids is approximately 5 μm. The spheroids thus obtained, are of homogeneous size and shape between the 4 lines but also within each of the lines.

Thus, the method of the invention allows the manufacturing of highly homogeneous ASC spheroids with a high degree of stability in culture. Changes of medium needs only the transfer of the seeded substrate material of the invention in a new cell culture vessel at the interface of a fresh culture medium, then reinforcing the very high stability of the newly made spheroids.

Example 3: Characterization of Spheroids Made from ASC

A main problem in the culture of spheroids is the formation of necrotic core in spheroids, therefore the cell viability of the ASC spheroids prepared according to the invention was investigated as described below. Further, the identity of the cells was controlled by immunostaining as described below.

Cell Viability

The viability of the spheroids was controlled using a fluorescent labelling kit (Ibidi) with fluorescein diacetate (FDA) and propidium iodide (PI) according to the supplier's instructions and then the spheroids (FIG. 5A1) were visualized by using an inversed fluorescence microscope. As shown in FIG. 5A2-4, after 48 hours, the FDA signal which label living cells is present in the majority of the cells, over the entire surface of the spheroid. In contrast, the cell death-associated PI is expressed with high intensity only on very few cells of the spheroid. Thus, a good cell viability after 48 hours and one week was observed in ASC spheroids prepared according to the invention.

Identity of the Cells

Spheroid immunostainings were done in suspension. The spheroids were first washed in PBS and then fixed with a 4% paraformaldehyde solution for 20 minutes at room temperature. The spheroids were then rinsed in PBS and resuspended in PBS supplemented with bovine serum albumin 1%, Triton X-100 0.3%. The spheroids were then incubated overnight at +4° C. with the primary anti-Strol Mouse IgM (LifeTechnologies). After three washes in PBS, incubation with Alexa555 secondary anti-Strol Mouse IgM (Invitrogen) was performed for 90 minutes. The Stro-1 expression in all the labelled spheroids was positive, suggesting that the cells in spheroids retain a stromal identity.

Next, cells were incubated in 100 μl of PBS supplemented with 10% of bovine serum albumin with each dilution of the antibodies 1. Isotype controls with the same fluorochrome were used. The cells and antibodies were incubated for 30 minutes at 4° C., washed with PBS and resuspended in PBS prior to analysis with a flow cytometer LSRFortessa™ (Becton Dickinson). Data analysis was done with the FlowJo software. This analysis of cell-surface markers by flow cytometry showed the expression of ASC markers (CD44, CD73, CD90, CD105) and the absence of markers that must be negative in ASC (HLA-DR, CD45, CD14) (FIG. 5B) in a monolayer of cells derived from spheroids (after one-week culture). It revealed a cell surface phenotype compatible with ASC after 9 days of spheroid culture and additional one week culture in monolayer.

In addition, a full transcriptome was analysed. Isolation of total RNA was performed by using RNeasy kit from Qiagen according to the manufacturer's instructions. RNA concentration was determined by a spectrometer (Thermo Scientific™ NanoDrop 2000) and RNA quality was verified by 2100 bioanalyzer (Agilent). For microarray analysis, it was performed with an Affymetrix chip targeting 21,448 mRNAs on the extracted RNA (Complete GeneChip® Instrument System, Affymetrix®, see World Wide Web: affymetrix-.com)

Figure 5:
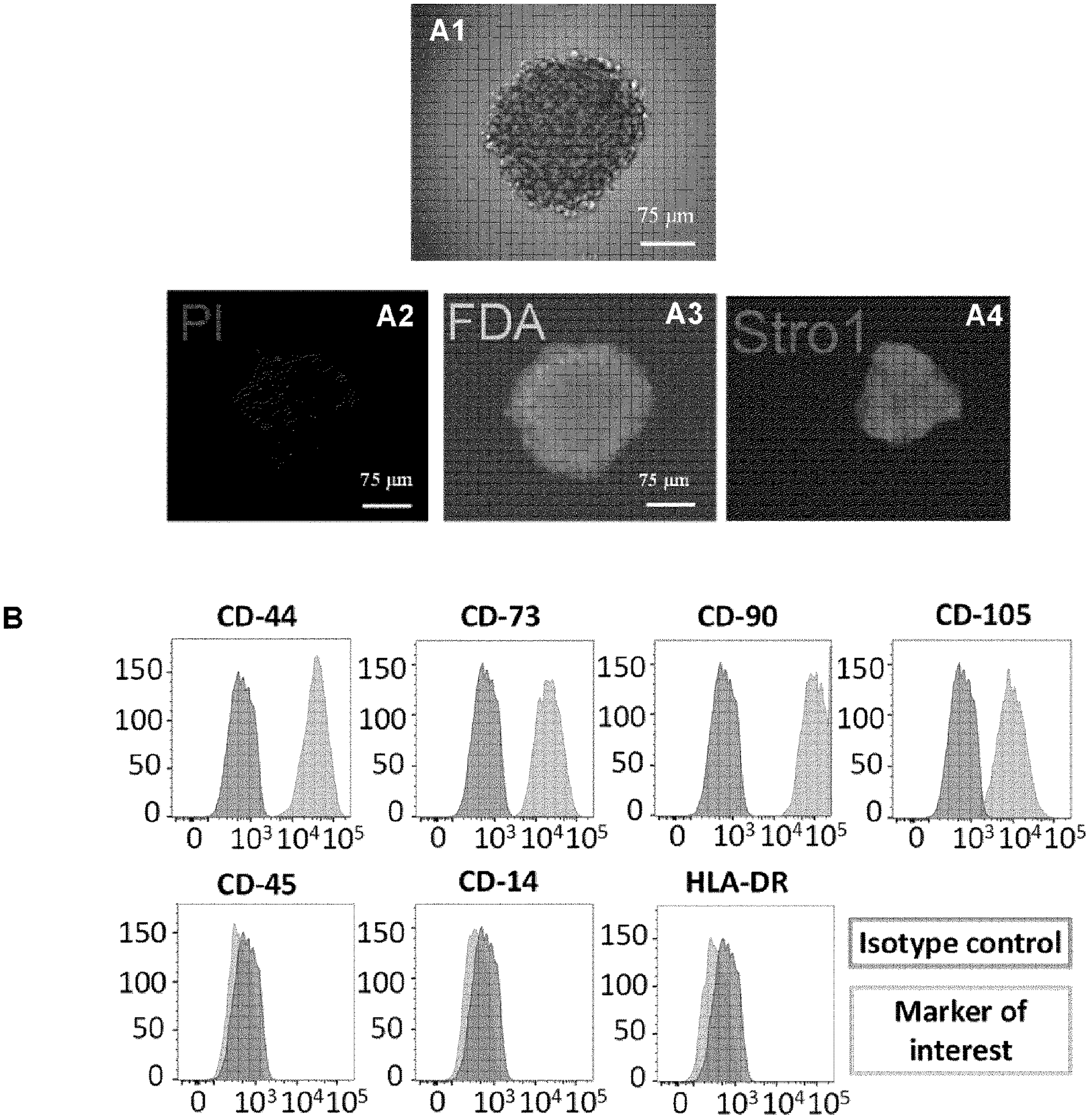
FIG. 5 shows the characterization of the viability and identity of spheroids made from ASCs according to the invention as described in Example 3. A1-A4: Light transmission picture (A1) and staining of spheroids made from ASC with Propidium Iodide PI (A2), Fluorescein diacetate FDA (A3) and Stro-1 (A4); B: Flow cytometric analysis of ASC markers in a cell line derived from spheroids plated on plastic in tissue culture plates. C: Comparison between spheroids and ASCs in 2D for the mRNA expression of markers used for ASC identification; D1-D3: Multilineage differentiation of a cell line derived from spheroids plated on plastic in tissue culture plates. Cells derived for spheroids were exposed to different media inducing differentiation towards adipocytes (FABP4) (D1), chondrocytes (Aggrecan) (D2) or osteocytes (osteocalcine) (D3).
Figure 5:
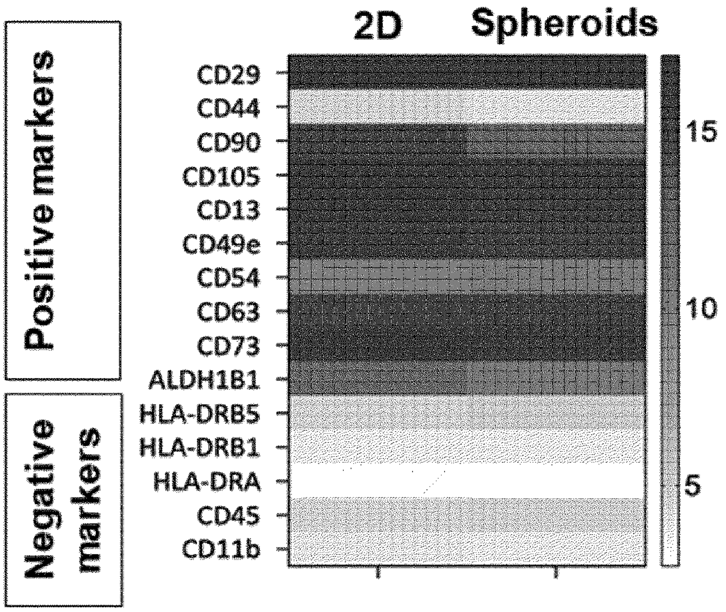
Figure 5:
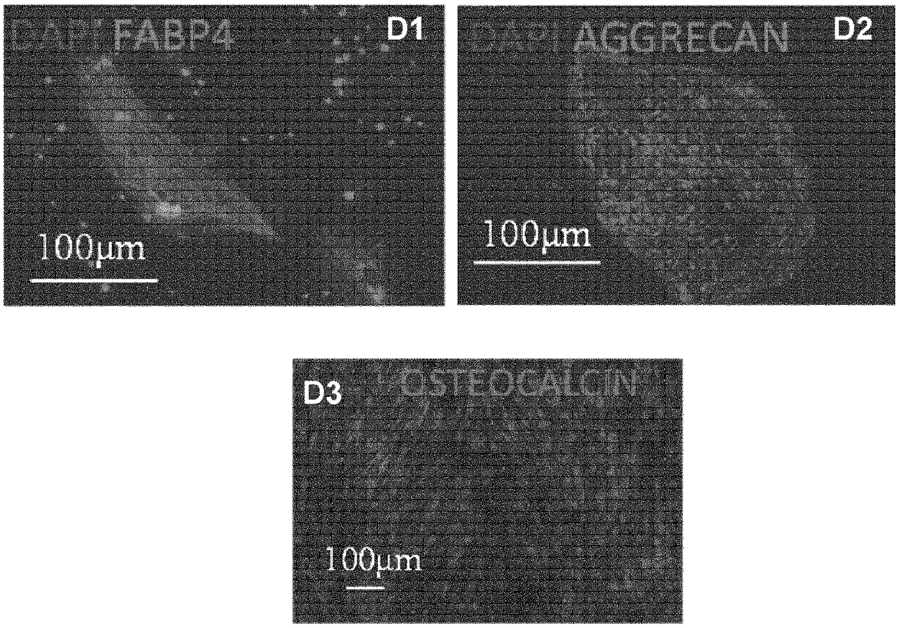

The mRNA of ASC markers was found in both spheroid and 2D conditions, with the exception of CD44 (FIG. 5C). As CD44 expression was seen in flow cytometry (FIG. 5B), this may be due to a weakness of CD44 detection in the microarray. Thus, cells in spheroids made from ASCs also harboured a gene expression profile compatible with ASCs.

Finally, multipotency of cells in spheroids made from ASC was tested as described below. A monolayer of cells was derived for one week from spheroids made from ASC and then differentiated, under appropriates media, towards adipocytes, chondrocytes and osteocytes. The three cell types were obtained, as seen by the expression of the adipocytic marker FABP4, chondrocyte marker (aggrecan)

and osteocyte marker (osteocalcin) (FIG. 5D). Thus, cell derived from spheroids made from ASC harboured the multipotent properties of ASC.

Characterization of Spheroids Made from ASC: Complete Gene Expression Profile

A heatmap and principal component analysis were performed on data generated using TAC4.0.1.36 software (Biosystems®) using the heatmap package. (see World Wide Web: cran.r-project.org/web/packages/pheatmap/index-.html) with default settings. A word cloud analysis was generated using an algorithm combining the statistical software R and the Gosummaries package.

Figure 6:
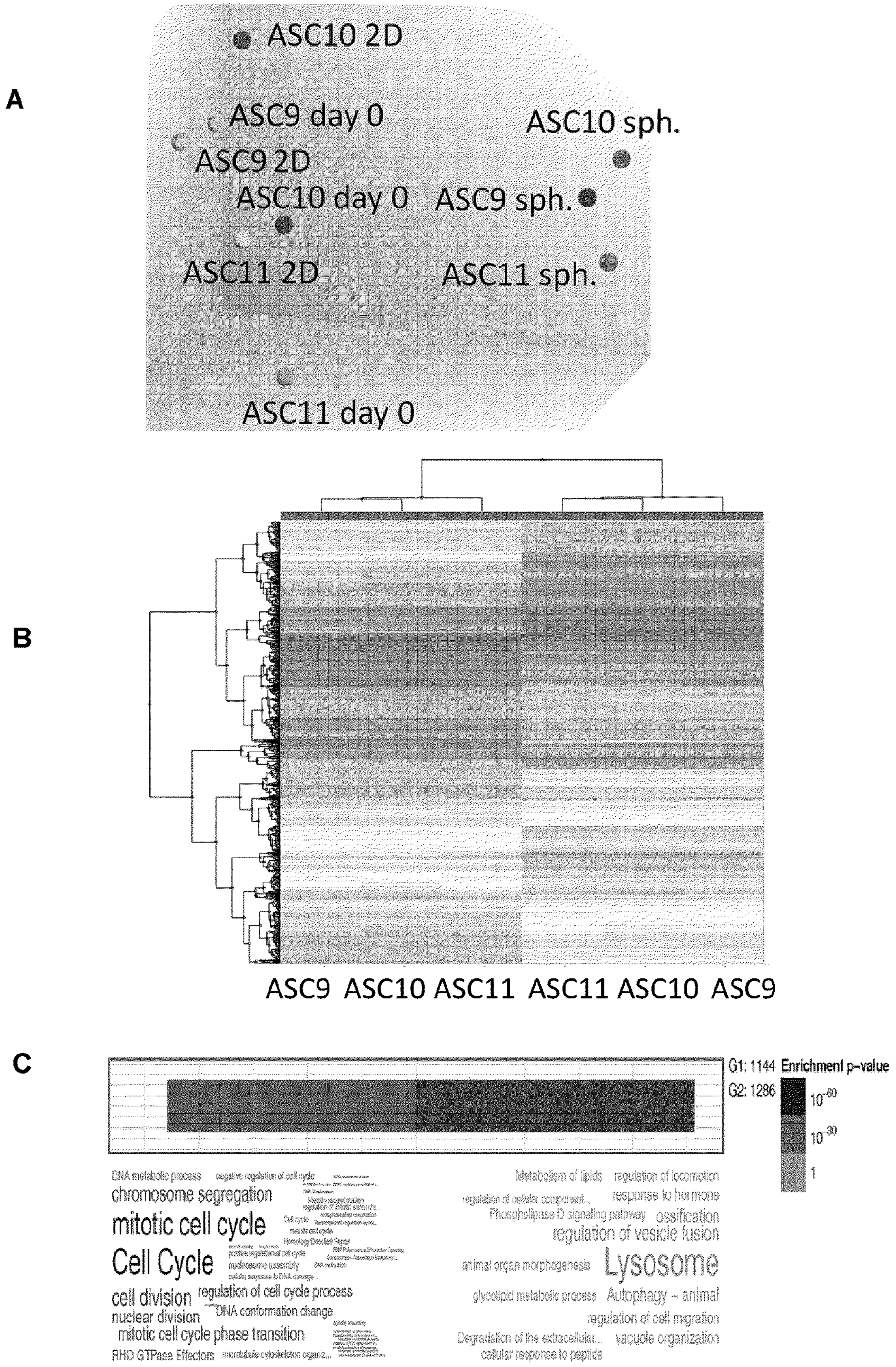
FIG. 6 characterizes the gene regulation in spheroids prepared according to a method of the invention compared to ASC in 2D as described in Example 3. A: Complete gene expression profile of ASC analyzed at day 0, or 48 h later in monolayer (2D) or spheroids, for three independent ASC lines (ASC9, ASC10, ASC11) and compared through a Principal Component Analysis; B: Hierarchical clustering of complete gene expression profiles of 2 days ASC in 2D or 2 days-spheroids derived from the same ASC. Three independent ASC lines are compared. C: Word cloud analysis of the significant regulations in gene expression comparing 2 days ASC in 2D or 2 days-spheroids derived from the same ASC. Three independent ASC lines are compared.

Total RNA extracted from 3 ASC lines (ASC9, ASC10, ASC11) were analysed on Affymetrix chip to compare the gene expression profile in spheroids versus ASC in 2D (culture at sub-confluence on a plastic surface), 48 h after spheroid formation. A Principal Component Analysis (PCA) showed that the gene expression profile of ASC in spheroids differed from ASC in 2D or before the analysis (=day 0) (FIG. 6A). Thus, ASC in spheroids regulate differently their gene expression than ASC cultured in monolayer. A Heatmap representing a global view of the level of expression of each transcriptome between the 2D and 3D ASC was also generated to analyse the results. The conditions studied were automatically ranked by the map generation software in order to group together the most concordant conditions. The heatmap (FIG. 6B) showed that the 2D ASCs and spheroid ASCs prepared according to the invention were automatically classified into two well-differentiated groups, confirming a gene regulation in spheroids compared to 2D. A wordcloud analysis to determine the functional nature of gene differentially expressed between spheroids and 2D was performed. Genes related to cell cycle and cell proliferation were down-regulated in spheroids whereas genes linked to autophagy (including lysosomal response) were up-regulated. These observations suggested that ASCs in spheroids reduced their proliferation compared to ASCs in monolayers where proliferation and cell passaging are constant. An autophagic response to stress without toxicity (confirmed by viability assays described above) is then suggested and could favor the angiocrine properties of ASCs. Indeed, autophagy is a major inducer of vessels formation (Hassanpour et al., 2018, *Stem Cell Res Ther.,* 9(1):305) and was shown to protect MSC from apoptosis under hypoxic conditions (Zhang et al., 2012, *Stem Cells Dev.,* 21(8): 1321-1332). Moreover, autophagic MSC secrete more VEGF, bFGF and angiogenin and thereby accelerate regeneration (Hassanpour et al., 2018, supra) whereas the inhibition of autophagy reduces their pro-angiogenic effects.

Figure 7:
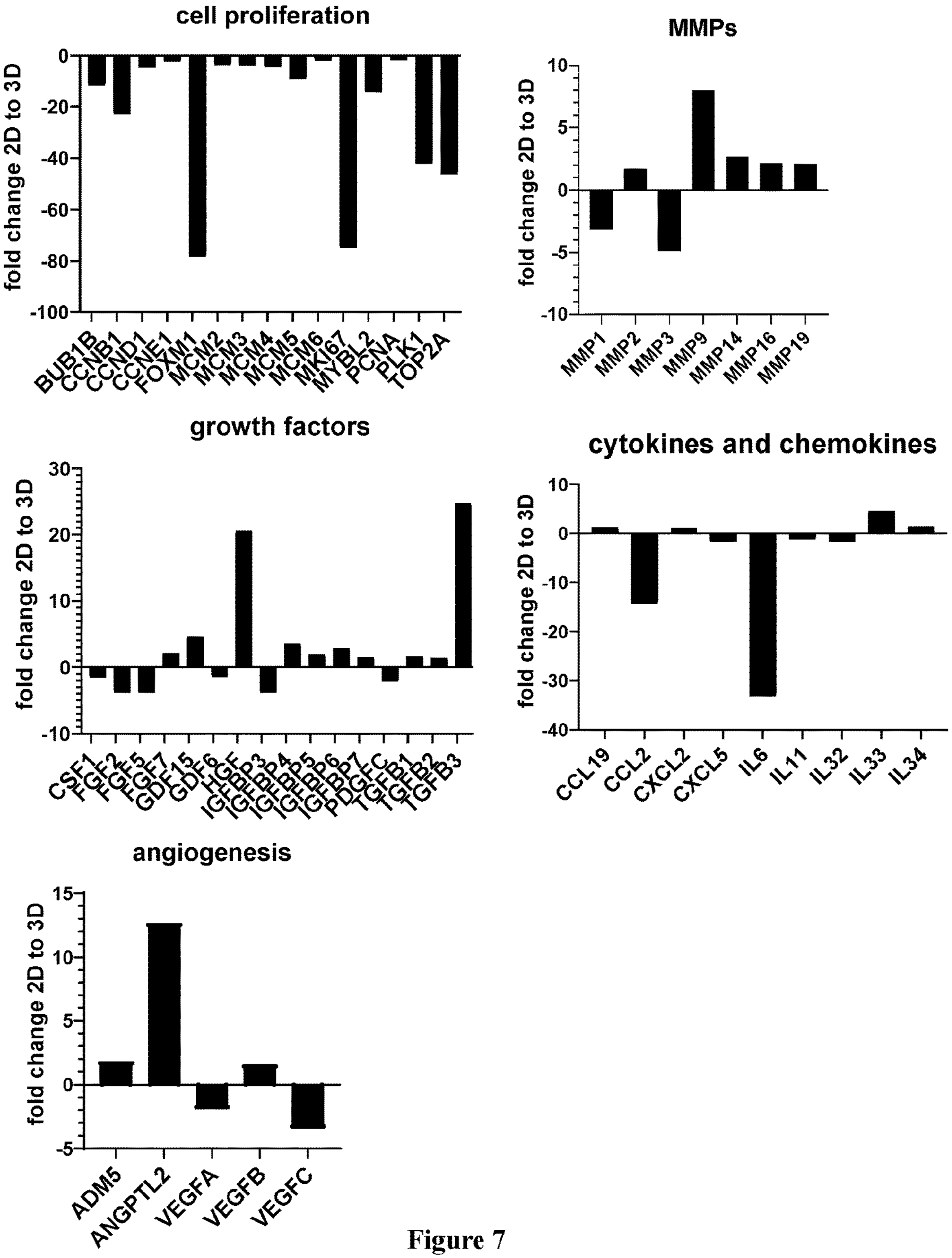
FIG. 7 represents the targeted screening of regenerative genes in 2 days-spheroids prepared according to the invention versus ASC in 2D as described in Example 3. Two hundred fifteen genes involved in regeneration were screened in transcriptomics data to identify the most significant regulations. The regulations considered to be significant based on the fold change (<2 or >2 with a significant p value) are presented here and classified according to their functions.
Figure 7:
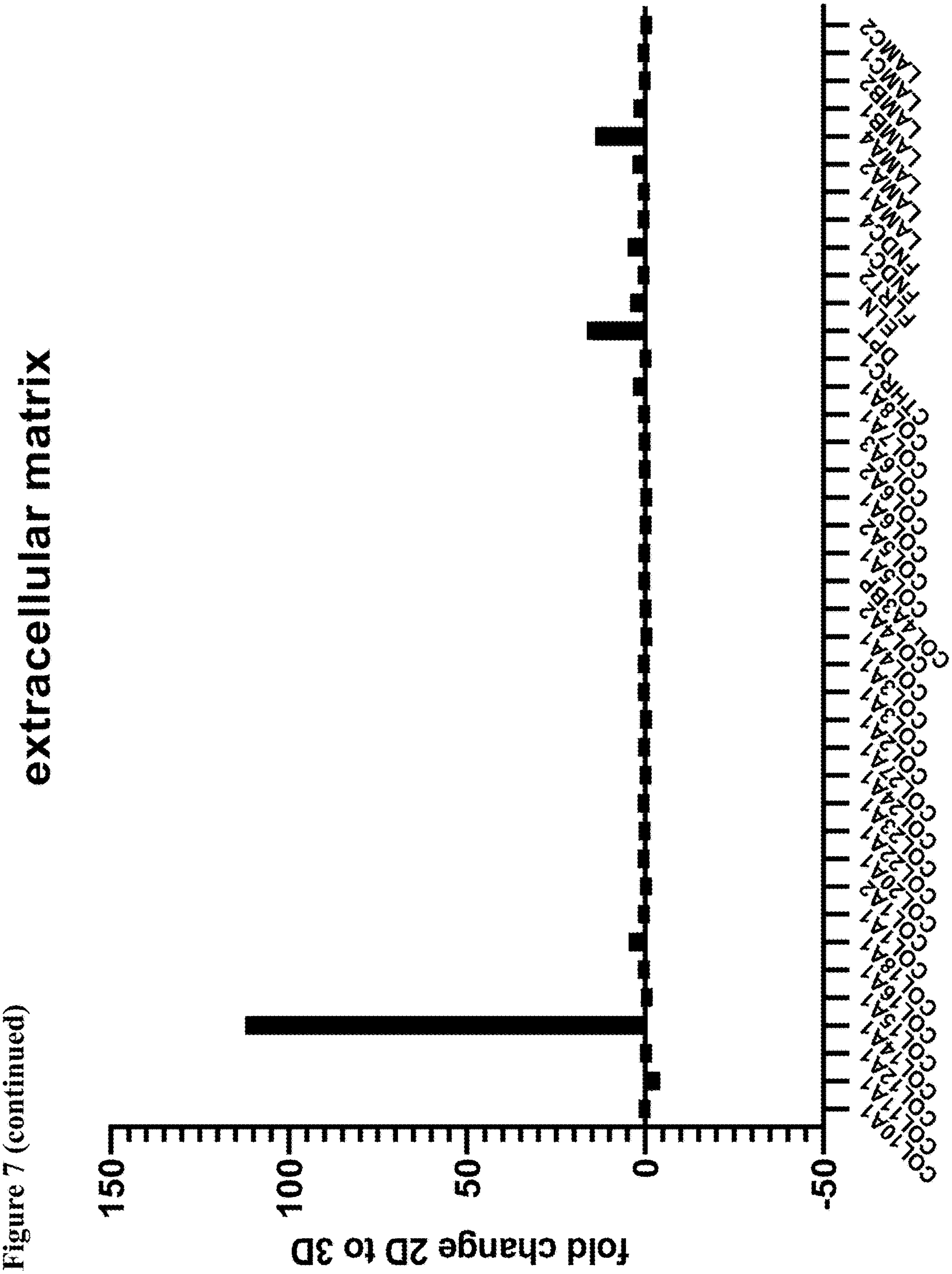

In addition, a screening by arbitrarily selecting genes (215 mRNA) theoretically involved in tissue regeneration, representing the fold change between 2D and 3D was carried out (FIG. 7). Almost all the genes responsible for cell proliferation were down-regulated in the spheroids, with a considerably strong regulation. Conversely, MMP9 and the angiogenic ANGPTL-2 were up-regulated. HGF and TGFβ3 were strongly up-regulated. The pro-inflammatory IL-6 and CCL-2, and neurotrophic NRG1 were, however, down-regulated. Genes coding for proteins of the extracellular matrix shows some spectacular up-regulations: Dermatopontin (DPT), laminin alpha-1 (LAMA4) and especially collagen 14 (COL14A1)). Together, these data mean the global maintenance of the expression of regenerative genes in the spheroids prepared by a method of the invention, with some noted regulations.

Characterization of Spheroids Made from ASC: Secreted Proteome

Cells in 2D or spheroids were washed with a serum-free DMEM (Thermofisher) and cultured at 37° C. in this free-serum medium overnight. Medium was collected and centrifuged at 500× g for 10 minutes to remove residual cells and free nuclei. Samples were then frozen at −80° C. Proteins were precipitated, digested and peptides were analyzed by nanoLC-MSMS using an easynLC1000 (Thermo Fisher Scientific) coupled with a Q Exactive HF mass spectrometer (Thermo Fisher Scientific). Database searches were performed with Mascot (Matrix Science) using the Human Reference Proteome database (Uniprot). Data were analyzed and validated with Scaffold (Proteome Software) with 1% of protein FDR and at least 2 unique peptide per protein with a 0.1% of peptide FDR.

Figure 8:
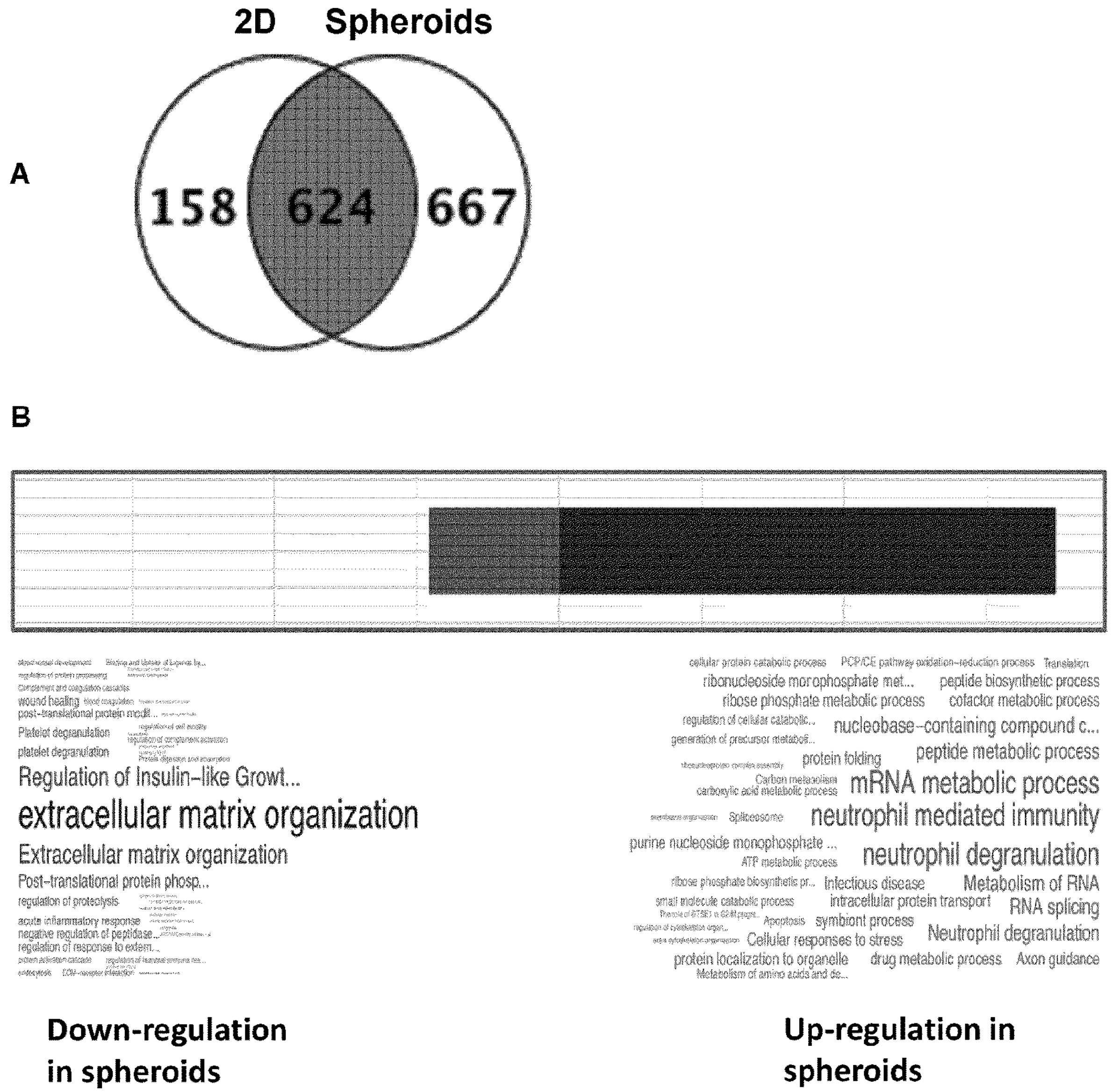
FIG. 8 represents the Analysis of the secreted proteome from spheroids according to the invention versus ASC in 2D as described in Example 3. A: ASC in 2D or spheroids were cultured in serum-free medium (=conditioned media) prior mass spectrometry analysis of its protein composition. The number of proteins identified in each sample is presented; B: Word cloud analysis of the most significant differences between conditioned media from spheroids and ASC in 2D.

Total proteins were extracted from the supernatant of 2 ASC lines (ASC 10, ASC 11) in 2D or spheroids (48 hours) cultured for 12 h in protein-free medium according to a method of the invention and analysed by mass spectrometry. The first difference noted was the total amount of proteins found in the cell supernatant. 15.51+/−1.4 µg of protein per cell was found in the 2D samples. In contrast, in spheroids samples, only 6.92+/−0.5 µg per cell were found, suggesting a barrier effect in the secretion proteins were cells are compacted. In contrast, mass spectrometry identified a larger protein diversity in the spheroid samples compared to the 2D: 1291 proteins were identified in the spheroids samples whereas 782 proteins in the 2D samples (FIG. 8A). Among them, 667 proteins were found only in the spheroid samples and 158 proteins were identified only in the 2D samples. Together, these observations show that the secretome of ASC grown in spheroids according to a method of the invention were enriched in their diversity, but quantitatively reduced by a barrier effect. A word cloud analysis of the proteins significantly up or down regulated in the ASC spheroids was performed (FIG. 8B). Among the up-regulated (or induced) proteins in spheroids, proteins linked to autophagy were confirmed. On the opposite, proteins involved in the organization of the extracellular matrix were significantly down-regulated, probably highly mobilized in the produced extracellular matrix between cells in spheroids.

Characterization of Spheroids Made from ASC: Biological Activity in a Pre-Clinical Model of Reconstructive Surgery The regenerative properties of ASC spheroids made through this solution were tested in a mouse model of fat transplantation which is the most recognized animal model for lipofilling: human fat subcutaneous transplantation in immunocompetent Balb/c mice as described below.

Animal Experimentations

Immunosuppressed animals cannot be used because the immune system and inflammation are a part of the whole regenerative process and fat immunogenicity remains very low, with a delayed time for complete xenorejection. 0.6 ml of human fat transplants were placed through fine 1.05 mm cannula under the scalp skin of BALB/cJ mice, with the addition of ASC in single cell suspension (2D) versus ASC spheroids versus control (vehicle alone). The fat was premixed with ASC spheroids or single suspension ASCs or saline buffer using a three-way valve. Throughout the study graft volumes were followed by in vivo micro-CT scan imaging (Quantum GX) under general anaesthesia and the data were analyzed by a post-processing software suite for image data (VivoQuant).

On the other hand, another experiment was carried out. In the same way as before, 0.6 ml of fat were injected with or without ASCs expressing luciferase. Throughout the experiment, graft volumes were monitored by micro-CT scan imaging under general anaesthesia. The CT-Scanner images were analysed as above and by IVIS image analysis software for the luminescence images.

Figure 9:
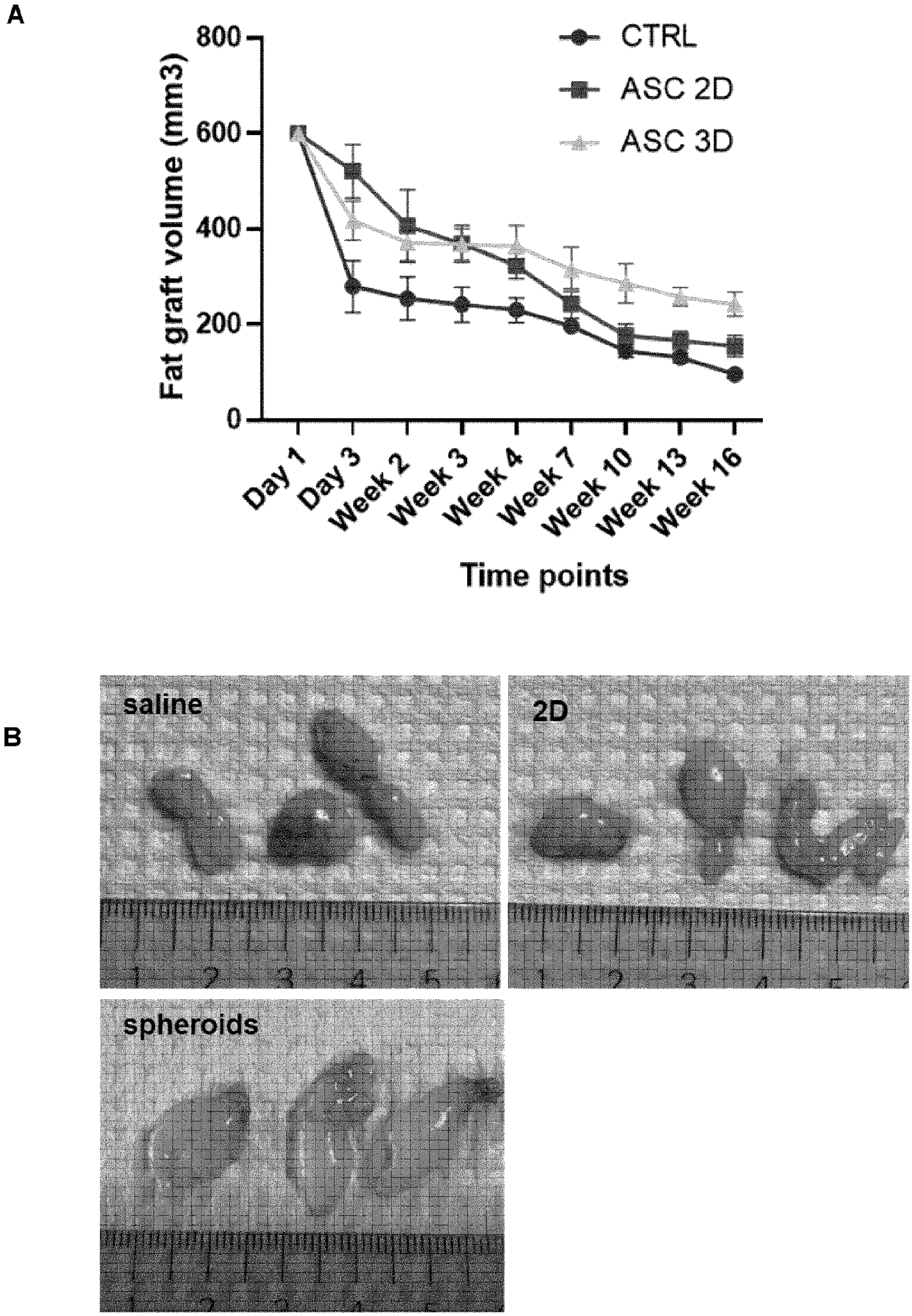
FIG. 9 illustrates the regenerative properties of spheroids of the invention in vivo in a model of fat transplantation for reconstructive surgery as described in Example 4. A: Groups of Balbc/J mice were transplanted subcutaneously (scalp) with human fat mixed with saline, ASC in 2D or spheroids according to the invention. The size was monitored after transplantation for 16 weeks by CT-Scan imaging; B: Picture of fat grafts 6 weeks post-transplantation.

ASC in 2D or spheroids prepared according to a method of the invention decreased the resorption of the transplant compared to vehicle alone (FIG. 9A). The long-term stability of transplants was increased with ASC spheroids of the invention compared to ASC in 2D starting at week 7 post-transplantation and maintained until week 16 post-transplantation. Macroscopically, fat transplants at day 16 were bigger with ASC spheroids compared to 2D and vehicle alone control that were similar (example of week 6, FIG. 9B). Thus, ASC spheroids made according to the invention induce more stable and long-term fat grafts in a mouse model of lipofilling. In conclusion, ASC spheroids produced by a method of the invention are confirmed to be more regenerative in vivo and could be used for lipofilling applications in reconstructive surgery.

Example 4: Manufacturing Human Pluripotent Stem Cells Spheroids on a Substrate Material of the Invention A method of the invention was used for the preparation of spheroids from human pluripotent stem cells and the obtained spheroids were compared to those obtained by immersion under agitation (3Di) after forced centrifugation in Aggewell-800.

Culture of Pluripotent Stem Cells

Culture of HS420 human embryonic stem cell line was done on Laminin-521(Thermofisher)-coated culture plates in Stemflex Medium (ThermoFisher), and 1% penicillin/streptomycin (thermofisher) at 37° C. and under 5% $CO_2$. Cells are passaged with enzymatic procedure (Accutase-Stemcell. To allow for better survival, re-plated cells at the desired density are exposed to Rho-associated protein kinase (ROCK) inhibitor (10 μM) for 24 h.

Manufacturing of Pluripotent Stem Cell-Derived Spheroids by Forced Aggregation Followed by Immersion (3Di)—Comparative Example HS420 cells were deposited in their medium in Aggrewell-800™ (Stemcell technologies, 6 well plate, 2 ml per well) at the ratio of 2'200 cells per microwell (the microwell plate used here contains 1,800 microwells per well). In order to correctly distribute the cells in each microwell, the plate is gently shacked and put on a stable support. After 15 min, the plate is cultured at 37° C. for 24 h to generate spheroids. 24 hours after spheroids formation, the culture medium is replaced with fresh maintenance medium without ROCK inhibitor and spheroids are transferred to 6 well-plate (standard condition, commercially available is then called 3D and immersion (3Di)), 2 ml of medium per well, and cultured at 37° C. and 5% Co2 under constant agitation (60 rpm, orbital shaker).

Manufacturing of Pluripotent Stem Cell—Derived Spheroids by a Method According to the Invention 2200 human pluripotent stem cells per microwell in their maintenance medium (Stemflex Medium (ThermoFisher), and 1% penicillin/streptomycin (thermofisher)) are deposited on a substrate material prepared according to Example 1 and containing 720 microwells per well (=1.6 million cells in 1 mL of maintenance medium containing ROCK inhibitor). In order to correctly distribute the cells in each microwell, the substrate material is gently shacked and put on a stable support for 15 min. Medium is then removed by aspiration with a 0.5×16 mm needle and spheroids are just covered by a thin film (10) of residual medium before incubation of the plate at 37° C. for 24 hours. 24 hours after spheroids formation, culture medium is replaced with fresh maintenance medium without ROCK inhibitor.

Figure 10:
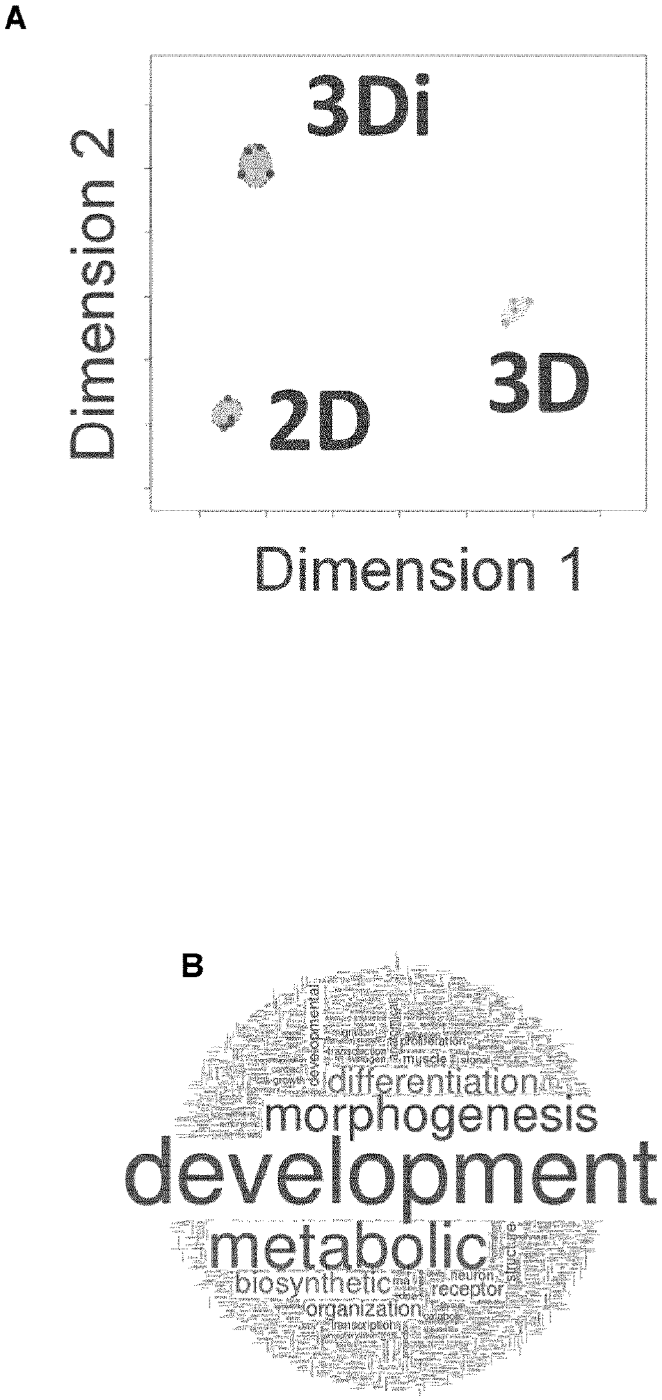
FIG. 10 presents the gene expression profile of PSC spheroids manufactured by forced aggregation followed by immersion in medium or through a method of the invention as described in Example 5. A: PSC spheroids were manufactured by forced aggregation followed by transfer in 6 well plate under agitation (=immersion=3Di) or by using the method of the invention (=3D); B: Word cloud analysis of the genes differentially expressed between 3Di and 3D. C: Up-regulation of some neuroectodermal genes in PSC spheroids made in 3Di versus the method of the invention.

RNA sequencing analysis compared PSC culture in monolayer, spheroids by using commercial forced aggregation followed by maintenance in immersion under agitation (3Di), spheroids by using our solution with air/liquid interface (3D). Four different batches of cells were tested. The first observation in this RNAseq analysis was that the method of cell culture has an effect on cells, because with a multidimensional scaling analysis 3 completely different populations with very close quadruplicates for each condition were obtained (FIG. 10A). To understand which are the biological process significantly changed between the 3Di and 3D, a word cloud analysis was carried out. In this analysis, it was interesting to observe that several biological processes were up-regulated in the 3Di such as the development, metabolic, morphogenesis and differentiation (FIG. 10B). To have a more precise vision of which biological pathways were regulated when the solution was used, a Gene Set Enrichment was conducted. This computational method determines whether an a priori defined set of genes show statistically significant enrichment at either extremity of a ranking list of differentially expressed genes. Resulting from this analysis, it was observed that between all the genes regulated, there are 34 significantly up-regulated and 62 down-regulated pathways with the solution compared with 3Di. Among them, pathways involved in the ectoderm, neural crest and neuronal differentiation were present in the list of the 15 more up-regulated pathways, as seen by the classification of their Normalized Enrichment Score (NES) and False Discovery Rates (FDR) (=probability to be a false positive value) (FIG. 10C). Thus, PSC spheroids made by a method according to the invention are regulated in favour of differentiation, especially neural differentiation.

Example 5: Manufacturing Neurospheres on a Substrate Material of the Invention Neurospheres derived from Pluripotent Stem Cells (PSCs) are widely used for many applications: healthy or diseased neural tissue modelling, drug screening and toxicity assays and possibly cell therapy applications in the future. A method of the invention was used for the preparation of neurospheres and the obtained neurospheres were compared to those obtained by commercially available Agrewell™-800 followed by immersion under agitation (3Di).

Manufacturing of Pluripotent Stem Cell—Derived Neurospheres by Forced Aggregation Followed by Immersion (3Di)—Comparative Example Pluripotent stem cell—derived spheroids are manufactured as described above (3Di). 24 hours after spheroids formation, the spheres are collected and then transferred in 6 well plates in DMEM-F12 medium supplemented with 1% N-2 supplement (Thermofisher), 1% of penicillin/streptomycin, 0.5 μM of SB431542 and 10 μM LDN193189 (dual-SMAD inhibition cocktail). Spheroids are then cultured under constant agitation in 2 ml of medium (60 rpm, orbital shaker). At day 8, medium is replaced by DMEM-F12 supplemented with 1% N-2, 1% B-27 supplement (Thermofisher) and bFGF (20 ng/ml). At day 21, the neurospheres are plated on polyornithine/laminine-coated tissue culture plates in maturation medium: 50% DMEM F12 with Glutamax, 50% Neurobasal medium, 1% B-27, 1% N-2, 1% Non-essential amino-acids, Beta-mercaptoethanol (0.1 mM), 1% penicillin/streptomycin, 20 ng/ml of Brain-derived neurotrophic factor (BDNF) and 20 ng/ml of Glial cell-derived neurotrophic factor (GDNF).

Manufacturing of Pluripotent Stem Cell—Derived Neurospheres by a Method According to the Invention Pluripotent stem cell—derived spheroids are manufactured as described above. 24 hours after spheroids formation, medium is changed: DMEM-F12 medium supplemented with 1% N-2 supplement (Thermofisher), 1% of penicillin/streptomycin, 0.5 μM of SB431542 and 10 μM LDN193189 (dual-SMAD inhibition cocktail). At day 8, medium is replaced by DMEM-F12 supplemented with 1% N-2, 1% B-27 supplement (Thermofisher) and bFGF (20 ng/ml). At day 21, the neurospheres are collected and plated on polyornithine/laminine-coated tissue culture plates in maturation medium: 50% DMEM F12 with Glutamax, 50% Neurobasal medium, 1% B-27, 1% N-2, 1% Non-essential amino-acids, Beta-mercaptoethanol (0.1 mM), 1% penicillin/streptomycin, 20 ng/ml of BDNF and 20 ng/ml of GDNF.

Immunofluorescence of Neurosphere-Derived Neurons

The cell on glass coverslips are washed in PBS and then fixed with a 4% paraformaldehyde solution for 30 minutes at room temperature. They are rinsed in PBS and replaced in PBS supplemented with bovine serumalbumin 1%, Triton X-100 0.3%. The cells are then incubated overnight at +4° C. with the primary anti-BetaIIITubulin Polyclonal Rabbit antibody (Biolegend-Covance). After three washes in PBS, incubation with Alexa555 secondary anti anti-BetaIIITubulin (Invitrogen) is performed for 90 minutes. Again, a step of three washes in PBS are performed before marking the nucleus staining with DAPI (300 nM). After 3 successive washes in PBS, cells are rinsed in pure water and fixed in Fluorsave mounting medium (Calbiochem). The samples are imaged with fluorescence microscope (ZEISS Axio2).

Electron Microscopy of Neurosphere-Derived Neurons

The cells are first washed in PBS and then fixed with a 4% paraformaldehyde solution for 30 minutes at room temperature. The cells are then rinsed in PBS and dehydrated in baths with successively increasing percentages of ethanol. Then, samples are left overnight in the fume hood to dry. Samples are covered with a 20 nm gold film using sputter coating HHV (Bangalore, India), and imaged in a sigma 300 VP FE-SEM (Field-emission SEM) from Zeiss (Oberkochen, Germany).

Figure 11A:
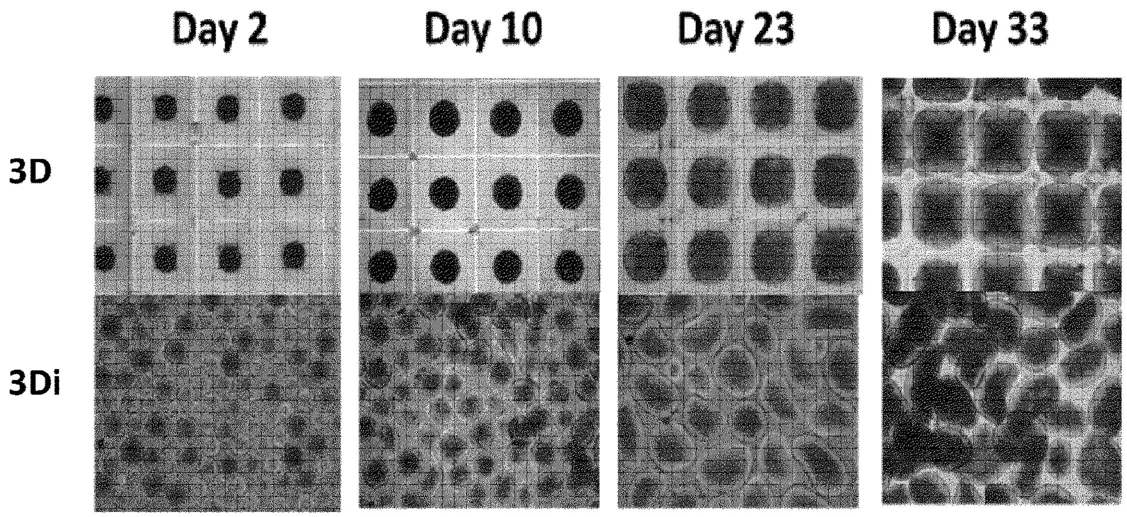
FIG. 11 compares PSC-derived neurospheres manufactured according to the invention with PSC-derived neurospheres manufactured by forced aggregation and immersion in medium as described in Example 6. A: Monitoring of the size and shape of PSC-derived spheroids according to the invention (3D) or after forced aggregation followed by immersion in medium (3Di). B: Software-based analysis of the distribution of areas, perimeters and diameters between PSC-derived neutrospheres manufactured according to the invention (3D) or after forced aggregation followed by immersion in medium (3Di).
Figure 11B:
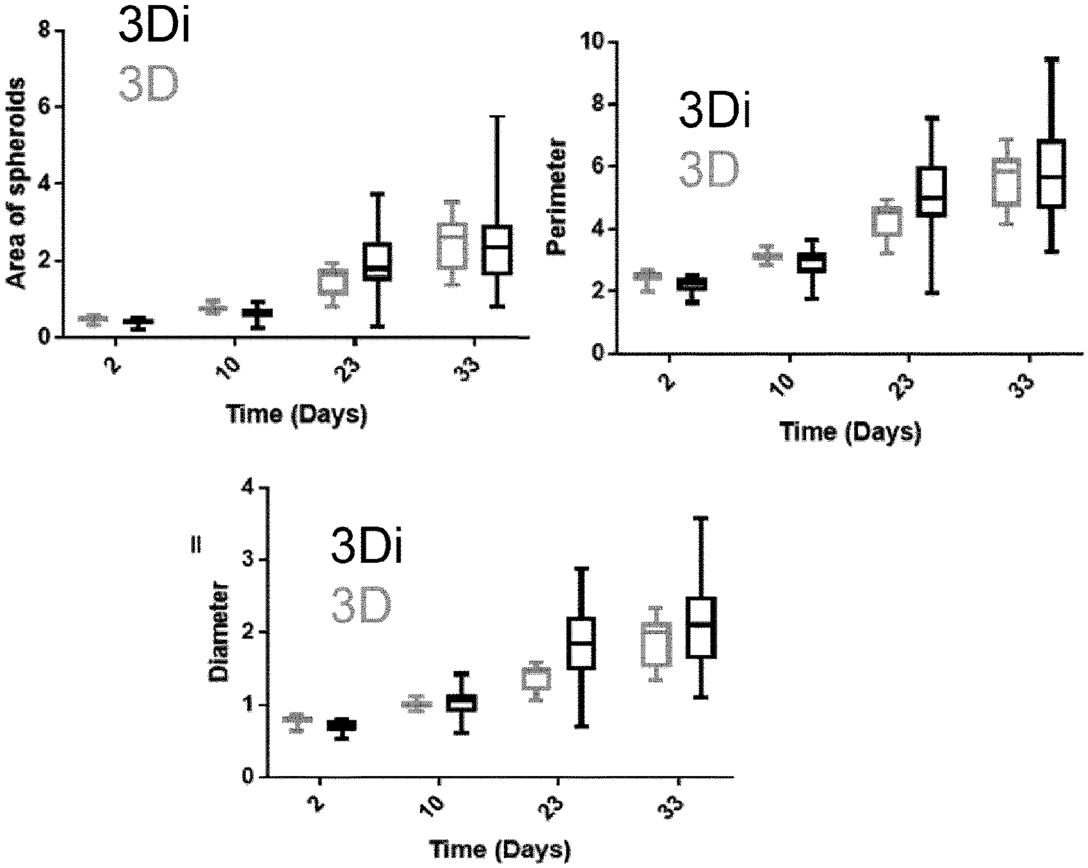
Figure 12:
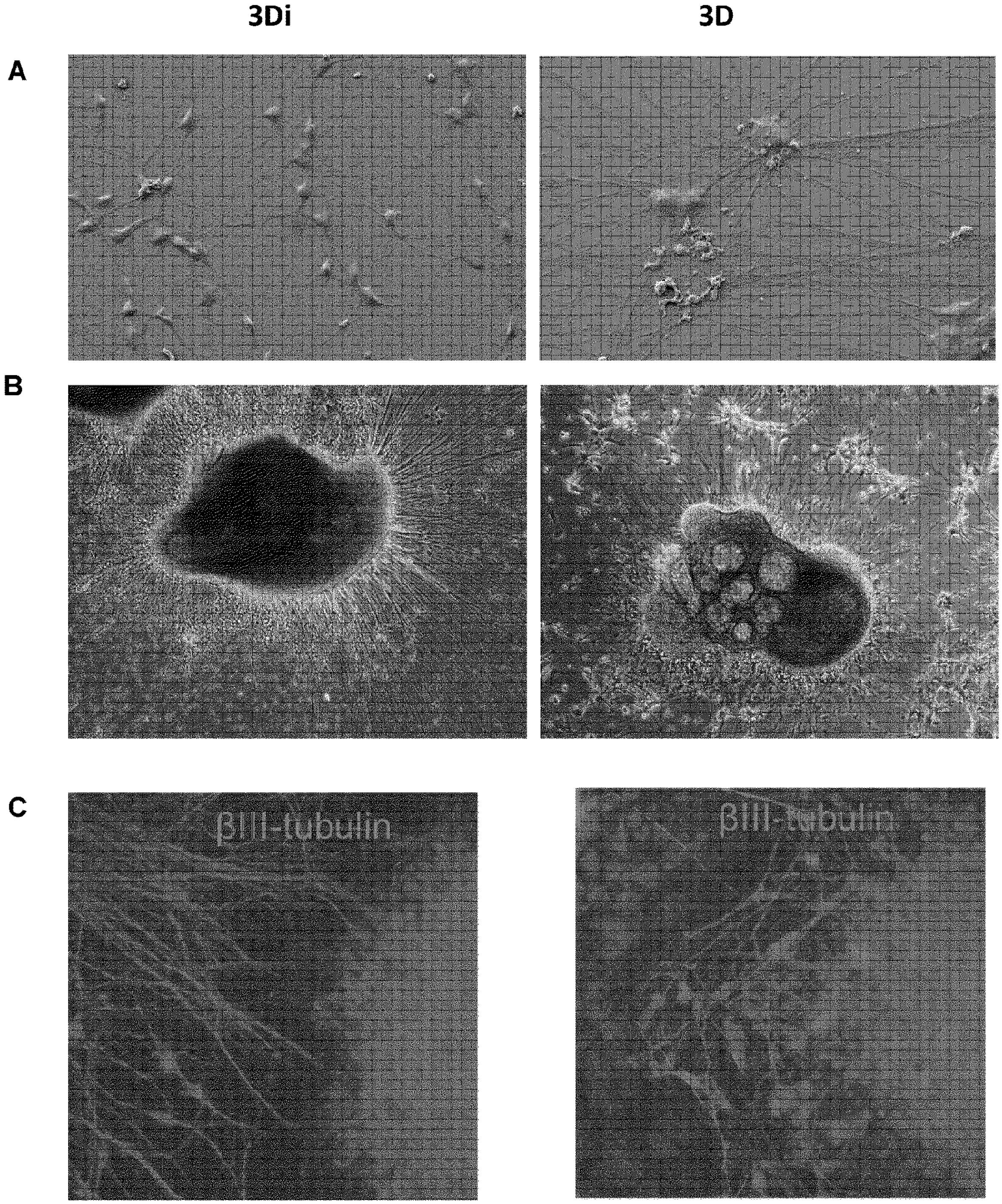
FIG. 12 shows PSC-derived neurospheres according to the invention terminally differentiated into neuronal cells. PSC-derived neurospheres are plated on polyornithine/laminin-coated tissue culture plates, in appropriated medium, after 3 weeks, for terminal maturation towards neuronal cells and derived neurons were analyzed by electron microscopy (A), inversed light microscopy (B) or immunofluorescence against the neuronal marker BIII-tubulin (C).

PSC Induced to Neurospheres by Using the Solution are More Homogeneous and Harbor a High Degree of Standardization Compared to Conventional Forced Aggregation Followed by Immersion Agitation A PSC-derived neurosphere culture was performed during 33 days and followed for the evolution of the size and shape of neurospheres by light microscopy. As shown in FIG. 11A, there was no early significant differences in both the round shape and size between the two methods. However, after 10 days of culture the neurospheres grown with the solution were more homogeneous than those grown on 3Di. FIG. 11A shows spheres at different time points. This high degree of standardization was confirmed by a software-based quantification of the range of the distributions of the area, perimeter and diameter (FIG. 11B) clearly lower for 3D. In addition, the spheroids, which initially have a round shape, kept their round morphology with the method of the invention, while those in 3Di evolved into more heterogeneous and elongated shapes. Neuronal maturation of neurospheres from both techniques was assessed on polyornithinine—laminin-coated plates at day 21. Electron microscopy (FIG. 12A), phase contrast microscopy (FIG. 12B) and immunofluorescence against the neuronal marker beta-III tubulin (FIG. 12C) show abundant neurons with both techniques, confirming that the method of the invention keeps the neural stem cell properties of produced spheroids.

Altogether, those data support the possibility to advantageously manufacture (simplification of the procedure and maintenance of culture, less culture medium required) highly standardized neurospheres (size & shape) according to a method of the invention and those advantageous property are expected to bring a strong benefit for all of the applications using neurospheres and neural transplants.

Figure 13:
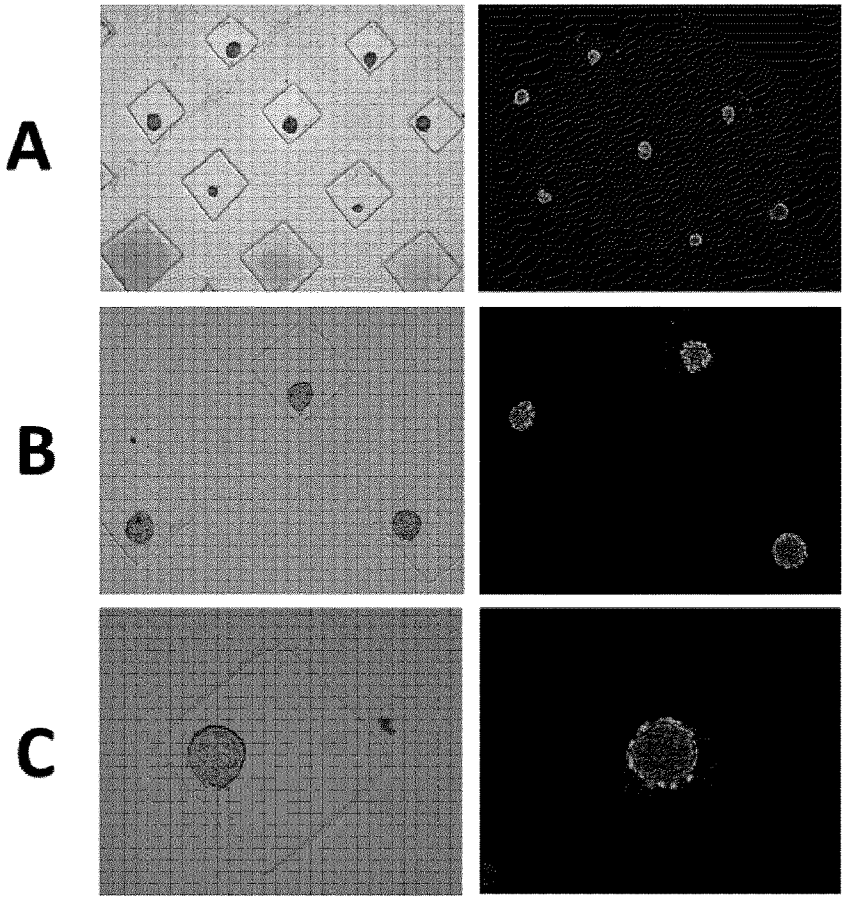
FIG. 13 shows frozen sections of microwells containing the spheroids photographed directly after (on the left) and after DAPI labeling of the nuclei (on the right) at different magnifications ×5 (A), ×10 (B) and ×20 (C), respectively, prepared as described in Example 6.

Example 6: Preparing Frozen Sections of Several Spheroids/Organoids on a Substrate Material of the Invention A substrate material according to the invention was used to prepare spheroids according to a method of the invention with 2000 cells per microwell cells as described in Example 4. The well-shaped indents of substrate material of the invention containing the formed spheroids were frozen directly in Milestone Cryoembedding Compound (MCC) and then cut with a cryostat to thicknesses ranging from 5 μm to 20 μm. The sections of a thickness of 5 μm were photographed directly after (photos on the left) and after DAPI labeling of the nuclei (on the right) at different magnifications ×5, ×10 and ×20, as shown on FIGS. 13A, B and C, respectively.

Those results show that a substrate material according to the invention allows to directly froze/cryopreserve the microwells containing the spheroids in order to carry out frozen sections/cryosections of several spheroids/organoids in the same plane and to carry out the various histological or immunohistochemical markings in succession.

Figure 14:
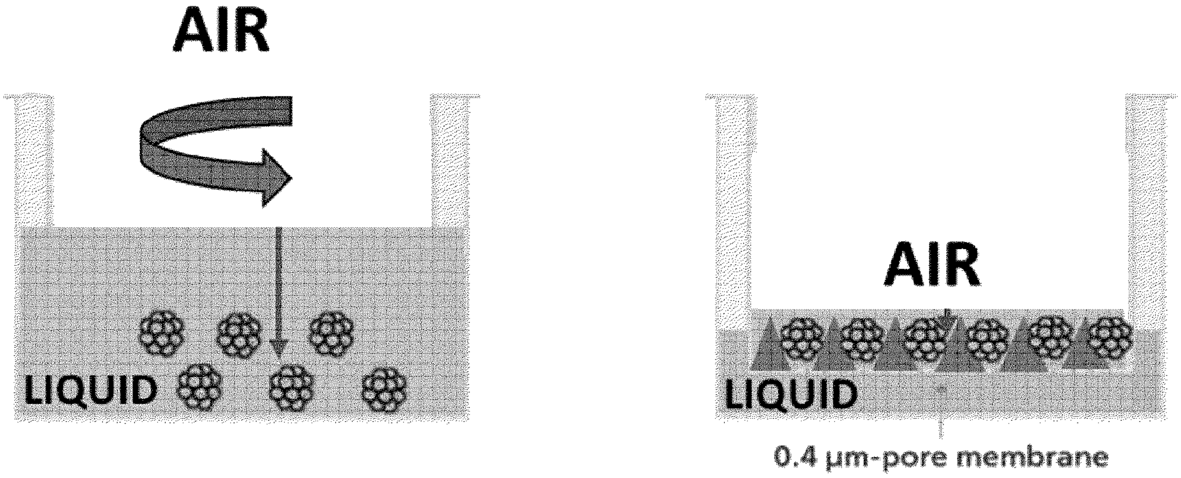
FIG. 14 is a schematic representation of the conditions of culture of dopaminergic spheroids as described in Example 7 for a standard method not from the invention (left) and for the method of the invention (right).

Example 7: Comparison of Properties of Dopaminergic Neural Spheroids Cultured in a 3D Conventional Culture "3D-Immersion" (3Di) Method and Those Cultured According to a Method of the Invention As a practical reminder, in the standard method "3D-Immersion", the spheroids are first forced aggregated in plastic microwells, then removed and transferred in standard culture plates maintained under agitation such as described in example 4 as schematized on FIG. 14 (left). In contrast, according to a method of the invention, the spheroids are forced to aggregation in well-shaped indents from a substrate material comprising a hydrophilic and porous material layer with a plurality of lasting well-shaped indents on its outer surface supported by a semipermeable membrane on its inner surface and wherein the semi-permeable membrane is supported by a support frame on its edge, on the surface of a culture medium such that the substrate material is floating on the surface of a culture medium. In contrast to 3D-Immersion, they are individually maintained into the microwells without any transfer, immersion and agitation. The spheroids are cultivated in Air liquid interface as schematized on FIG. 14 (right) into the microwells at the surface of the semi-permeable/porous membrane and are covered with a nano-film of medium and directly exposed to the air. The semipermeable membrane allows their long-term stability and also establish air/liquid interface conditions that favors gas exchanges with air, allowing higher oxygen entry into the cells.

The distance between the air and the cells is significantly reduced allowing high diffusion oxygen and maintenance of the oxygen percentage applied by the incubator or cell-culture parameters. This system avoids limiting the $O_2$ supply for some cells and inducing hypoxia.

In the present case, the cultures were carried out with dopaminergic neural spheroids and the hydrophilic and porous material layer with a plurality of lasting well-shaped indents on its outer surface used as a substrate material of the invention was agarose as described in Example 4. At the end of dopaminergic differentiation, total RNA from spheroids cultured by the invention method or by the standard method was extracted. A complete transcriptome was analyzed. Total RNA isolation was performed using the Qiagen RNeasy kit according to the manufacturer's instructions. RNA concentration was determined by a spectrometer (Thermo Scientific™ NanoDrop 2000) and RNA quality was verified by the 2100 Bioanalyzer (Agilent). Transcriptomic analysis to assess gene expression was performed by RNAseq on 3 independent experiments.

Figure 15:
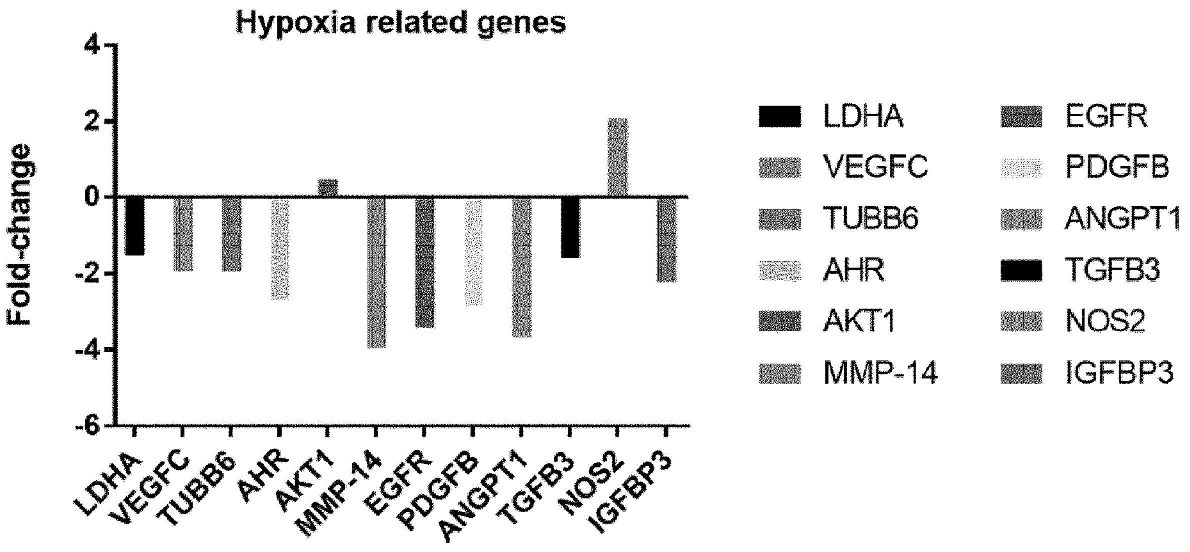
FIG. 15 represents gene expression fold change of hypoxia related genes between dopaminergic neuronal spheroids cultivated in immersion (comparative method not of the invention) and in air-liquid interface culture in a method according to the invention as described in Example 7 at week 6. Positive bars mean up-regulation in a method of the invention and inversely negative bars mean up-regulation in 3D-Immersion.

An up-regulation of hypoxia-related genes expression (as described in Examples 3 and 4) is observed in spheroids cultured with the 3D-Immersion method (FIG. 15).

Therefore, those data clearly support that a method and a substrate material according to the invention advantageously allows to avoid cell hypoxia which is at the origin of the formation of necrotic cores even in classical 3D methods.

Example 8: Stability and Morphology Comparison of Dopaminergic Spheroids Prepared by 3D-Immersion and Those Prepared by a Method According to the Invention The morphology and homogeneity of dopaminergic neural spheroids was studied over 5 months for comparing those obtained with a 3D conventional culture "3D-Immersion" as described in Example 7 with those obtained by a method according to the invention.

For this purpose, a dopaminergic differentiation was carried out. HS420 (pluripotent stem cells) were induced towards dopaminergic cells. Dual-SMAD inhibition (LDN-193189, a BMP signalling inhibitor as described in PubChem Compound Summary for CID 54613581 from National Center for Biotechnology Information, LDN-193189 monohydrochloride under World Wide Web: pubchem.ncbi.nlm.nih.gov/compound/LDN-193189-monohydrochloride. +SB-431542, selective inhibitor of ALK5/TGF-β type I Receptor as described in PubChem Compound Summary for CID 4521392 under World Wide Web: pubchem.ncbi.nlm.nih.gov/compound/sb-431542 from National Center for Biotechnology Information was applied for neural induction, FGF-8 (fibroblast growth factor 8), SHH (Sonic hedgehog protein), CHIR 99021 as described in PubChem Compound Summary for CID 9956119 under World Wide Web: pubchem.ncbi.nlm.nih.gov/compound/chir-99021 from National Center for Biotechnology Information, purmorphamine were used as factors for dopaminergic specification. For the neural differentiation and for neuronal maturation AMPC (Cyclic adenosine monophosphate), BDNF, GDNF, TGFB3 (transforming growth factor beta 3), FGF20 (Fibroblast growth factor 20) and Compound E were added in the neurobasal medium but by removing CHIR for the maturation step starting from day 13 as described in Cossetat al., 2019, J. Vis. Exp., (148), e59682, doi: 10.3791/59682.

Then, the evolution of the size and shape of the obtained dopaminergic neural spheroids was followed by light microscopy during 19 weeks. Photos of the spheroids were taken every week by an optical microscope at ×4 magnification, then analyzed by a software called ImageJ™.

Figure 16:
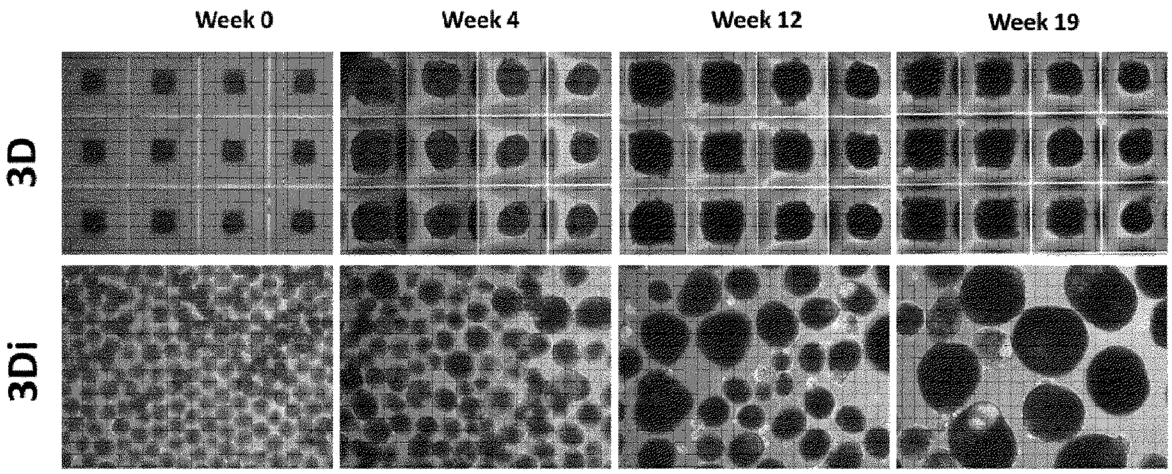
FIG. 16 represents light microscopy images of dopaminergic spheroids cultivated and kept viable, stable and functionally active until week 19 of culture as described in Example 8 wherein dopaminergic spheroids are according to the invention (3D) and compared to those cultivated in a comparative method (3Di), not from the invention.

As shown in FIG. 16, there was no significant difference in both the round shape and size between the two methods on the week 0. However, after 19 weeks of culture, the dopaminergic neurospheres grown according to the invention were more homogeneous than those grown on 3D-Immersion which were fused and more heterogenous and irregular in shapes.

The invention claimed is:

1. A method for the preparation of a substrate material for cell culture, said method comprising the following steps:

a) providing a semipermeable membrane supported by a support frame on its edges;

b) forming a malleable layer of a hydrophilic and porous material on said semipermeable membrane to form a composite matrix;

c) pressing a hydrophobic die comprising a plurality of tapered protuberances into an outer surface of the malleable layer of hydrophilic material of said composite matrix to form a plurality of well-shaped indents in said layer; and d) removing the die from the layer of hydrophilic material to obtain an imprinted composite matrix comprising a hydrophilic material layer with a plurality of lasting well-shaped indents on its outer surface supported by a semipermeable membrane on its inner surface.

2. The method according to claim 1, wherein the semipermeable membrane is a membrane comprising at least one material selected from polytetrafluoroethylene, polycarbonate, polyethylene terephthalate, cellulose esters, polystyrene sulfonate and polypropylene or a combination thereof.

3. The method according to claim 1, wherein the hydrophilic and porous material is a hydrophilic gel made from a polymer selected from carbohydrates, proteins, extracellular matrix (ECM) components, peptides, and mixtures thereof, or a gel derived from natural ECM or synthetic derived materials selected from poly(ethylene glycol), polyaliphatic polyurethanes, polyether polyurethanes, polyethylene copolymers, polyamides, polyvinyl alcohols, poly(ethylene oxide), polypropylene oxide, polyethylene glycol, polypropylene glycol, polytetramethylene oxide, polyvinyl pyrrolidone, polyacrylamide, poly(hydroxy ethyl acrylate), poly(hydroxyethyl methacrylate), and mixtures thereof or from a polymer selected from agarose, Polyvinyl(alcohol) (PVA), agar-agar, alginates, hyaluronic acid, pectin or starch or the like.

4. The method according to claim 1, wherein the imprinted composite matrix comprises a hydrophilic polymer layer with a plurality of lasting well-shaped indents on its outer surface supported by a semipermeable membrane on its inner surface, wherein the well-shaped indents have an aperture from about 100 $\mu m^2$ to 10 $cm^2$, a depth from about 100 μm to 40 mm, and a bottom surface area from about 0 $\mu m^2$ to 1 $mm^2$.

5. A method for the preparation of spheroids, said method comprising the following steps:

(i) providing a spheroid culture medium in a cell culture vessel;

(ii) placing a substrate material comprising a hydrophilic and porous material layer with a plurality of lasting well-shaped indents on its outer surface supported by a semipermeable membrane on its inner surface and wherein the semi-permeable membrane is supported by a support frame on its edge, on the surface of a culture medium such that the substrate material is floating on the surface of a culture medium;

(iii) contacting a cell suspension with the surface of the floating substrate material until cells form spheroids on the surface of the floating substrate material.

6. The method according to claim 5, wherein the substrate material comprises an imprinted composite matrix comprising a hydrophilic material layer with a plurality of lasting well-shaped indents on its outer surface supported by a semipermeable membrane on its inner surface.

7. The method according to claim 5, wherein the cells are stem cells selected from MSC, ASC, PSC, iPS, neurospheres, hepatospheres, cardiomyocytes, lung epithelium, or keratinocytes.

* * * * *